US012326622B2

(12) United States Patent
Lipson et al.

(10) Patent No.: US 12,326,622 B2
(45) Date of Patent: Jun. 10, 2025

(54) THERMALLY TUNABLE LOW BROADBAND WAVEGUIDES AND RELATED SYSTEMS AND METHODS

(71) Applicants: The Trustees of Columbia University in the City of New York, New York, NY (US); COLD SPRING HARBOR LABORATORY, Cold Spring Harbor, NY (US)

(72) Inventors: Michal Lipson, New York, NY (US); Aseema Mohanty, New York, NY (US); Mohammad Amin Tadayon, Bronx, NY (US); Adam Kepecs, Cold Spring Harbor, NY (US); Qian Li, Cold Spring Harbor, NY (US); Xingchen Ji, New York, NY (US); Christine P. Hendon, Bronx, NY (US); Xinwen Yao, New York, NY (US)

(73) Assignees: The Trustees of Columbia University in the City of New York, New York, NY (US); Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 16/480,973

(22) PCT Filed: Jan. 25, 2018

(86) PCT No.: PCT/US2018/015265
§ 371 (c)(1),
(2) Date: Jul. 25, 2019

(87) PCT Pub. No.: WO2018/140615
PCT Pub. Date: Aug. 2, 2018

(65) Prior Publication Data
US 2019/0391415 A1    Dec. 26, 2019

Related U.S. Application Data

(60) Provisional application No. 62/450,158, filed on Jan. 25, 2017, provisional application No. 62/451,504, filed on Jan. 27, 2017.

(51) Int. Cl.
*G02F 1/01* (2006.01)
*A61N 5/06* (2006.01)

(52) U.S. Cl.
CPC ......... *G02F 1/0147* (2013.01); *A61N 5/0601* (2013.01); *A61N 5/0622* (2013.01);
(Continued)

(58) Field of Classification Search
CPC ... G02F 1/0147; A61N 5/0601; A61N 5/0622; A61N 2005/063
(Continued)

(56) References Cited

U.S. PATENT DOCUMENTS 5,073,024 A    12/1991 Valette et al.
7,203,387 B2    4/2007 Doan
(Continued)

FOREIGN PATENT DOCUMENTS

EP    3020450 A1    5/2016

OTHER PUBLICATIONS

Buzsáki et al., "Tools for Probing Local Circuits: High-Density Silicon Probes Combined with Optogenetics", Neuron, vol. 86, Issue 1, Apr. 8, 2015, pp. 92-105.
(Continued)

*Primary Examiner* — Nicole F Lavert
*Assistant Examiner* — Naveed R. Kolia
(74) *Attorney, Agent, or Firm* — BakerHostetler

(57) ABSTRACT

Provided are devices that have a distal portion configured to be implanted in a brain of a subject. The distal portion
(Continued)

includes one or more emitters configured to emit light in the visible spectrum. The device includes a proximal portion configured to be external to the brain of the subject while the distal portion is implanted, wherein the proximal portion includes at least one waveguide in optical communication with the one or more emitters. The at least one waveguide defines a cross-sectional width less than 500 nm. The at least one waveguide is optionally coupled to a heating element that is optionally configured to adjust a phase of light within the at least one waveguide.

16 Claims, 15 Drawing Sheets

(52) U.S. Cl.
CPC ........ *G02F 1/011* (2013.01); *A61N 2005/063* (2013.01); *G02F 2203/50* (2013.01)

(58) Field of Classification Search
USPC .......................................... 607/92
See application file for complete search history.

(56) References Cited

U.S. PATENT DOCUMENTS

| | | | |
|---|---|---|---|
| 8,554,022 | B1 | 10/2013 | Hochberg et al. |
| 8,936,630 | B2 | 1/2015 | Denison et al. |
| 9,238,150 | B2 | 1/2016 | Deisseroth et al. |
| 10,004,917 | B2* | 6/2018 | Li .................. A61N 5/0622 |
| 2005/0047702 | A1 | 3/2005 | Parker et al. |
| 2008/0306576 | A1 | 12/2008 | Boyden et al. |
| 2011/0112591 | A1 | 5/2011 | Seymour et al. |
| 2011/0230747 | A1 | 9/2011 | Rogers et al. |
| 2012/0253261 | A1 | 10/2012 | Poletto et al. |
| 2013/0085398 | A1 | 4/2013 | Roukes |
| 2014/0142664 | A1* | 5/2014 | Roukes ............... A61N 5/0622 607/88 |
| 2014/0362433 | A1* | 12/2014 | Adams ................ H01S 5/0265 359/344 |
| 2015/0125111 | A1 | 5/2015 | Orcutt et al. |
| 2015/0196773 | A1 | 7/2015 | Brown et al. |
| 2016/0303384 | A1 | 10/2016 | Sahin et al. |
| 2018/0173024 | A1* | 6/2018 | McGreer ............... G02F 1/225 |

OTHER PUBLICATIONS

Fercher et al., "Optical coherence tomography", J. Biomed. Opt., vol. 1, No. 2, Apr. 1996, pp. 157-173.

Lipson et al., "Brain Eager: A Nanophotonic Platform for Multisite Optical Activation in the Brain", NSF Grant #: 1611090, https://www.nsf.gov/awardsearch/showAward?AWD_ID=1611090 &HistoricalAwards=false. [Only Abstract available].

Moss et al., "New CMOS-compatible platforms based on silicon nitride and Hydex for nonlinear optics", Nature Photonics, vol. 7, Jul. 2013, pp. 597-607.

Pisanello et al., "Multipoint-emitting optical fibers for spatially addressable In vivo optogenetics", Neuron, vol. 82, Issue 6, Jun. 18, 2014, pp. 1245-1254.

Raval et al., "Nanophotonic phased array for visible light image projection", 2016 IEEE Photonics Conference, Oct. 2016, pp. 206-207.

Renishaw plc. Interferometry explained., https://www.renishaw.com/en/interferometry-explained-7854.

Segev et al., "Highly Multiplexed Nanophotonic Probes With Independently Controllable Emitters for Optogenetic Brain Stimulation", Conference on Lasers and Electro-Optics, JTh4B. Jun. 2, 2016.

Tadayon et al., "Integrated nanophotonic platform for high bandwidth and high resolution optogenetic excitation", 2016 Conference on Lasers and Electro-Optics, Jun. 2016, pp. 1-2.

Heideman RG et al., Performance of a highly sensitive optical waveguide Mach-Zehnder interferometer immunosensor, Sensors and Actuators B: Chemical vol. 10 / Issue 3, pp. 209-217, Feb. 1993.

Liu Q et al, Highly sensitive Mach-Zehnder interferometer biosensor based on silicon nitride slot waveguide, Sensors and Actuators B: Chemical vol. 188, pp. 681-688, Nov. 2013.

Misiakos K et al, All-silicon monolithic Mach-Zehnder interferometer as a refractive index and bio-chemical sensor, Optics Express vol. 22 / Issue 22, pp. 26803-26813, Nov. 2014.

Prieto, F et al, An integrated optical interferometric nanodevice based on silicon technology for biosensor applications, Nanotechnology vol. 14 / Issue 8 pp. 907-912, Jul. 2003.

Yursever G et al, Photonic integrated Mach-Zehnder interferometer with an on-chip reference arm for optical coherence tomography, Biomed Opt Express, vol. 5/Issue 4, pp. 1050-1061, Apr. 2014.

* cited by examiner

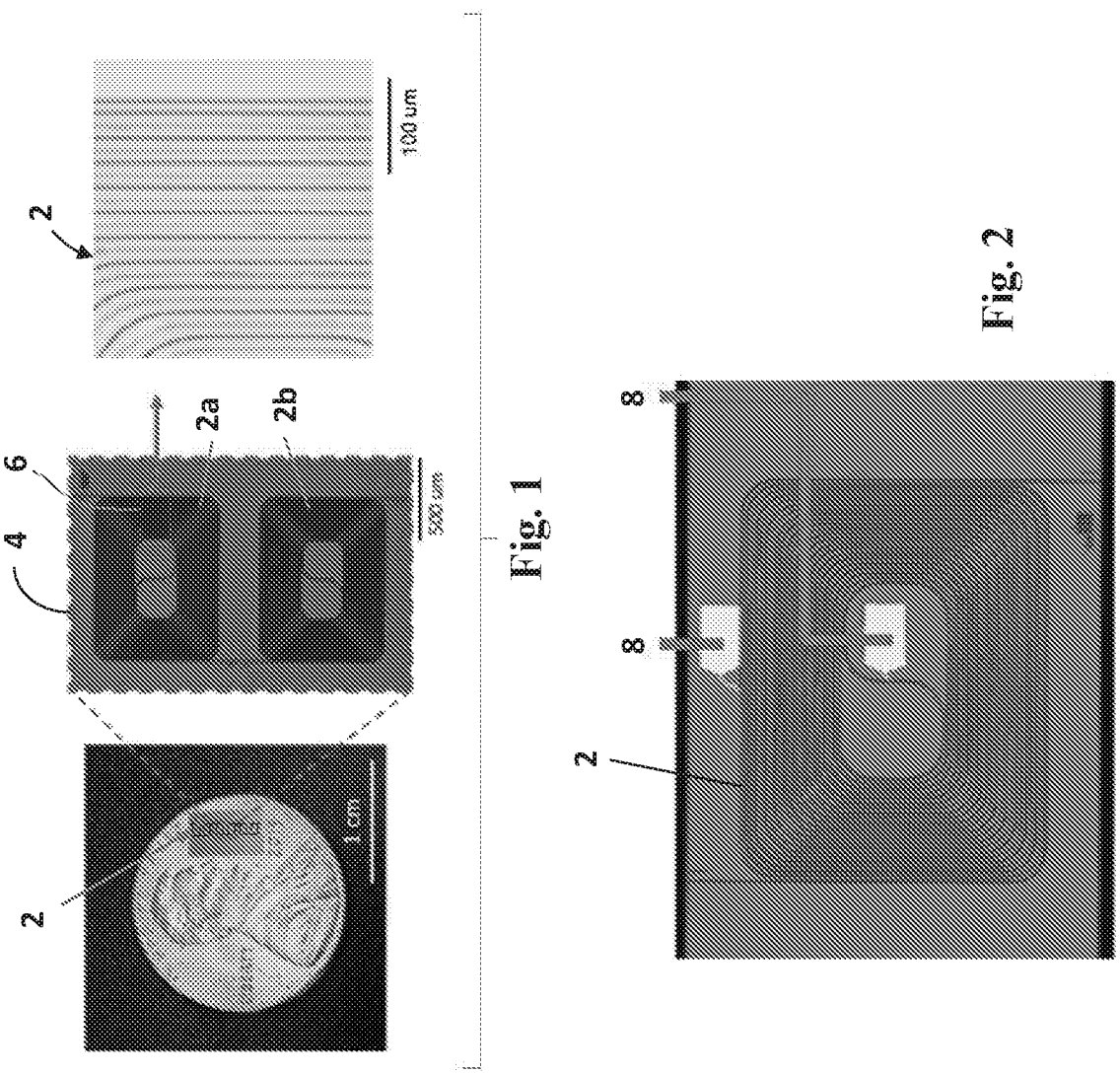
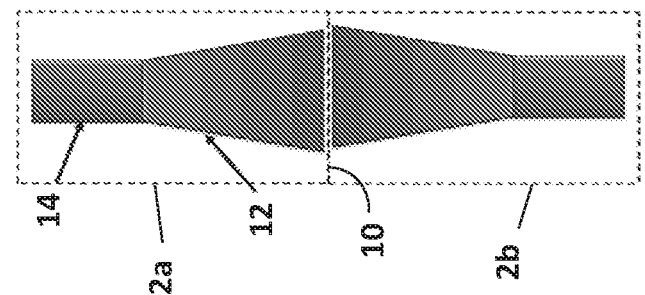

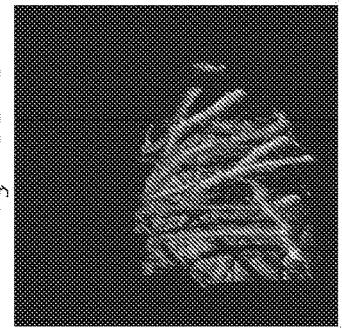
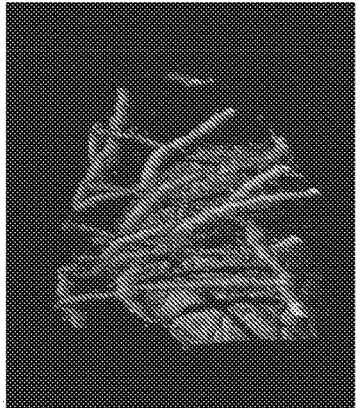
Fig. 16
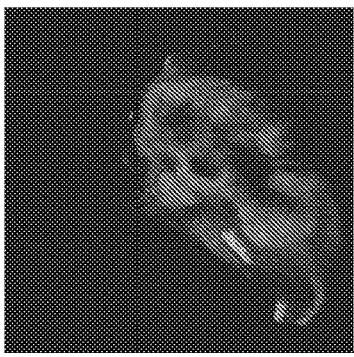
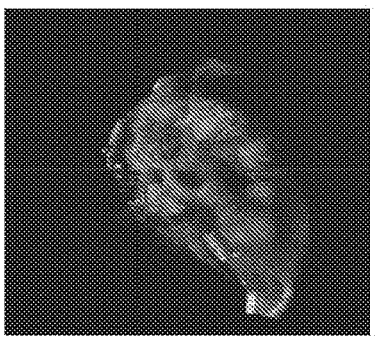
Fig. 17

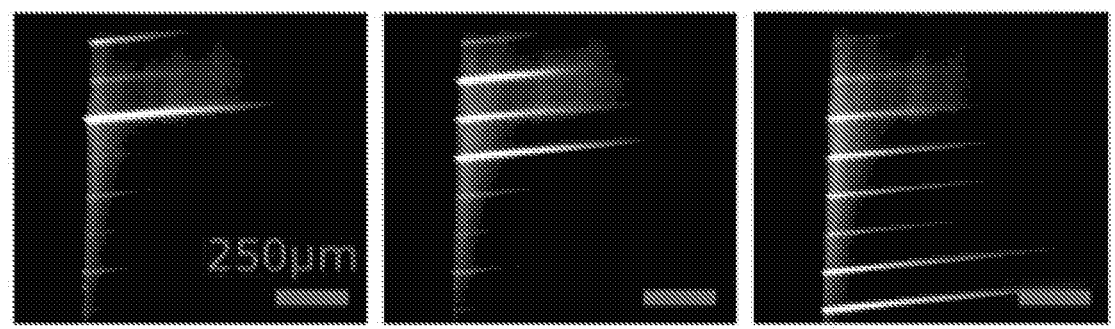
Fig. 21
Fig. 22
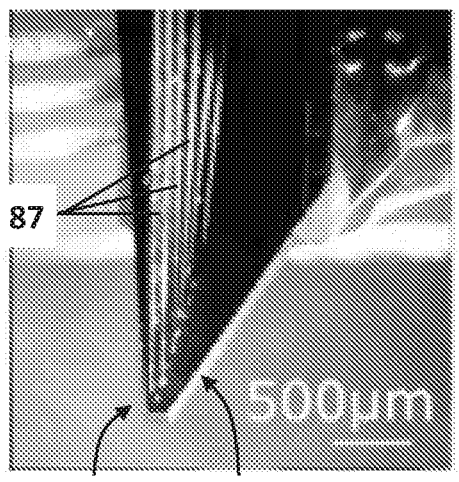
61  70
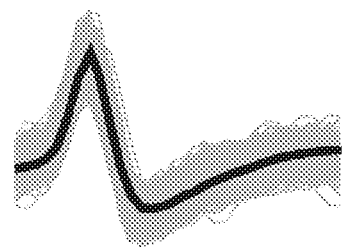
Spontaneous spike
Light evoked spike
R = 0.947
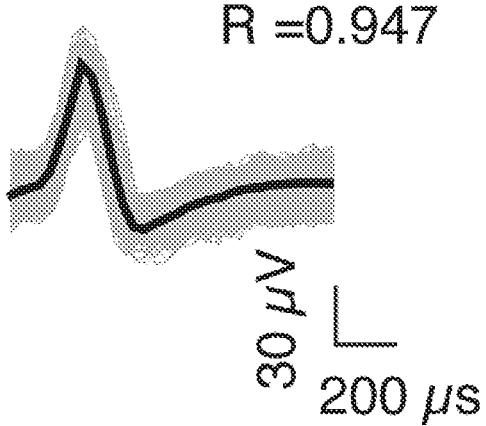
Fig. 23
30 μV | 200 μs

THERMALLY TUNABLE LOW BROADBAND WAVEGUIDES AND RELATED SYSTEMS AND METHODS

CROSS-REFERENCE TO RELATED APPLICATIONS

This application is the National Stage Application of International Patent Application No. PCT/US2018/015265 filed Jan. 25, 2018, which claims priority to U.S. Provisional Patent Application Ser. No. 62/450,158, filed on Jan. 25, 2017, entitled "Thermally Tunable Low Loss Broadband Waveguides and Related Systems and Methods", and to U.S. Provisional Patent Application Ser. No. 62/451,504, filed Jan. 27, 2017, entitled "Active Visible Devices Using a Thermally Tunable $Si_3N_4$ Photonic Platform for Optogenetic Applications, both of which applications are incorporated herein by reference in their entireties for any and all purposes.

GOVERNMENT RIGHTS

This invention was made with government support under Contract No. N66001-15-1-4052, awarded by the Defense Advanced Research Projects Agency; and Contract No. 1611090, awarded by the National Science Foundation. The government has certain rights in the invention.

TECHNICAL FIELD

The present disclosure relates to micro-scale and nano-scale photonic structures, devices and probes employing such structures, and related systems and methods.

BACKGROUND

Optical waveguides are employed in a wide variety of optical devices, including such devices that are sized within the nano-scale, and thus are of great interest in the fields of nanophotonics (also termed "nano-optics"), optics, optical engineering, electrical engineering, and nanotechnology. Nanophotonic devices are presently advancing a multitude of technologies and fields of research within the optical arts, including such technologies as Optical Coherence Tomography (OCT) and such fields as optogenetics, just to name a few.

Optical Coherence Tomography (OCT)

OCT imaging systems commonly employ interferometers that include a sample arm and a reference arm. Most reference arms are either based on fiber or individual free space optical components that limit the stability, cost and size of the respective systems, and do not have the capability to be precisely tuned.

Spectral Domain OCT ("SD-OCT") instruments typically have an imaging range from about 1 to 3 mm, which is sufficient to meet the requirements of many ophthalmology and cardiology applications. Other applications, however, such as full eye imaging and other industrial imaging applications, often require a longer imaging range that is normally beyond 1 cm.

Swept-Source OCT ("SS-OCT") systems offer some advantages, and some efforts have been made to develop ultra-high speed, centimeter-class swept-source (SS) lasers, which enables long-range SS-OCT imaging. A drawback of such an approach, however, is that the bandwidth of SS-OCT at wavelengths above 1 µm is usually limited to 100 nm to 150 nm, and as a result, the achievable axial resolution is constrained. Further, the amount of data generated by the foregoing technique increases drastically (up to several Gb/s) in order to maintain high resolution over the ultra-long imaging range. Such vast amounts of data requires advanced hardware implementation and high-performance data streaming, storage, and processing tools for real-time visualization. These requirements pose significant hurdles to the adoption of the SS-OCT technique in the field.

In terms of high resolution imaging, SD-OCT is known to be superior to SS-OCT because of the non-swept, broadband light sources for SD-OCT allow bandwidth above 150 nm and better phase stability. However, SD-OCT is inferior to SS-OCT in terms of high-speed imaging and signal roll-off. The speed of SD-OCT is fundamentally limited by the line-scan camera, and the signal roll-off is determined by the performance of focusing components in the spectrometer. Recently, a state-of-art InGaAs line scan camera has been demonstrated to allow a 120 kHz A-line rate, which is almost comparable to the SS-OCT source. However, the signal roll-off still remains a problem, and can negatively impact the performance of SD-OCT systems in some applications where the target of interest extends deep into the tissue. Strategies that can overcome this limitation of SD-OCT would greatly benefit applications where the targeted samples have high topology and concurrent high resolution imaging is desired.

Optogenetics

The ability to activate and inhibit neural populations using optogenetics has revolutionized the study of neural circuits; however, there is still no implantable optical device that has high enough resolution to test the spatial and temporal precision of neural encoding. Minimally invasive implantable probes that can both read and stimulate neural activity with such precision are necessary to understand how the brain encodes information while an animal performs a task or exhibit a behavior. There has been extensive development of implantable electrical recording tools that read neural activity with single neuron resolution and sub-millisecond precision at large volumes. However, current implantable optical stimulation technologies based on tapered fibers and micro-LEDs have been limited to studies with low spatial resolution (>100 micron) and temporal frequencies lower than 15 Hz.

Nanophotonics have the potential for manipulating light at sub-micron resolution and GHz time scales and can be integrated with electronic recording sites. However, active, reconfigurable nanophotonic devices are currently limited to the near-infrared regime. In the visible wavelength regime, interferometric structures become difficult to construct because the fabrication tolerances become tighter due to the shorter wavelength range and the lack of tunable materials. Thus, nanophotonic devices for the visible wavelength regime currently rely on passive structures that often require external table-top optics that are typically bulky, inefficient, and slow (longer than 1 ms). Light in the blue spectral range (wavelength of 473 nm) is particularly of interest for activating expression of ChR2 in genetically modified subjects, such as mice, but existing approaches are not sufficient for consistent and safe delivery of illumination to a subject's neurological systems.

SUMMARY

In meeting the described challenges, the present disclosure provides a device that includes: a distal portion configured to be implanted in a brain of a subject. The distal portion includes one or more emitters configured to emit light in the visible spectrum. The device includes a proximal portion configured to be external to the brain of the subject while the distal portion is implanted, wherein the proximal portion includes at least one waveguide in optical communication with the one or more emitters. The at least one waveguide defines a cross-sectional width less than 500 nm. The at least one waveguide is optionally coupled to a heating element that is optionally configured to adjust a phase of light within the at least one waveguide.

Also provided are methods, the methods comprising illuminating neural tissue of a subject with a device according to the present disclosure.

In another aspect, the present disclosure provides waveguides for electromagnetic waves, comprising: an optical path written into a pattern, the pattern including a plurality of segments of the optical path and a plurality of stitch boundaries therein, wherein at each of the stitch boundaries at least one of the segments of the optical path is stitched together with another of the segments of the optical path, and, at at least some of the stitch boundaries, the optical path defines an outward taper having a maximum width greater than a width of the optical path at portions of the associated segments remote from the at least one of the stitch boundaries.

Also provided are microchips, the microchips comprising a waveguide according to the present disclosure.

Additionally provided are methods, the methods comprising directing electromagnetic radiation through a waveguide according to the present disclosure.

The present disclosure also provides methods of refurbishing an optical system, the methods comprising replacing a reference arm of the optical system with a waveguide according to the present disclosure.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 1 is a schematic view of an exemplary waveguide according to an embodiment of the present disclosure;

FIG. 2 is a magnified view of a portion of the waveguide of FIG. 1, showing micro-heaters incorporated into the structure for thermally tuning the waveguide, according to an embodiment of the present disclosure;

FIG. 3 is a schematic view of field boundaries of a waveguide made according to an embodiment of the present disclosure;

FIG. 16 shows a 3D, high-topology, high signal-to-noise ratio (SNR) stitched OCT image (made using the presently disclosed technology) revealing human skin covered by gauze;

FIG. 17 shows a 3D, high-topology, high signal-to-noise ratio (SNR) stitched OCT image (made using the presently disclosed technology) of an aorta;

FIG. 21 shows side view microscope images of light exciting the probe of FIG. 18 and illuminating a fluorescent in various patterns determined by respective switch configurations;

FIG. 22 is a view of the distal tip of the probe of FIG. 18;

FIG. 23 shows a measured comparison between a spontaneous neural spike waveform and a light-activated neural spike waveform using a probe similar to that shown in FIG. 18;

DETAILED DESCRIPTION OF ILLUSTRATIVE EMBODIMENTS

Figure 4:
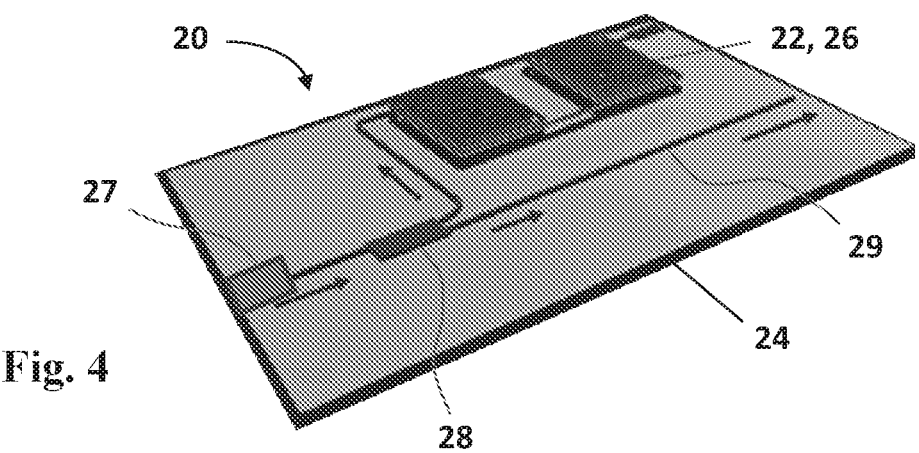
FIG. 4 is a schematic view of an on-chip OCT imaging system employing a waveguide as a reference arm, according to an embodiment of the present disclosure.

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable, and it should be understood that steps may be performed in any order.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. In addition, the term "comprising" should be understood as having its standard, open-ended meaning, but also as encompassing "consisting" as well. For example, a device that comprises Part A and Part B may include parts in addition to Part A and Part B, but may also be formed only from Part A and Part B.

Thermally tunable waveguides, preferably those made of silicon nitrides ($Si_3N_4$ or SiN), offer solutions to a host of challenges impeding devices and systems in the fields of optics and electronics, particularly those challenges encountered by integrated photonics and nanophotonics. By using low-loss silicon nitride waveguide(s) with high mode confinement, the thermo-optic effect the silicon nitride can be made highly efficient and can be utilized to control the refractive index of the waveguide by thermally adjusting the spatial dimensions of the waveguide. Of particular interest are thermally influenced adjustments to the effective length of the waveguide (and thus to the length of the optical path defined by the waveguide).

For example, the thermo-optic coefficient $\varepsilon$ of $Si_3N_4$ is about $2.45\pm0.09\times10^{-5}$ RIU/° C. Therefore, the optical path length in $Si_3N_4$, calculated as $l_{OPL}=(n_0+\varepsilon\cdot T)\cdot l_0$, can be extensively adjusted responsive to thermal input (i.e., "thermal tuning"), particularly when the effective length of the $Si_3N_4$ waveguide $l_0$ is tens of centimeter long or longer.

Referring now to FIG. 1, a waveguide 2 formed of $Si_3N_4$ and defining an optical path length of about 42 cm can be miniaturized according to the embodiments disclosed herein so as to be confined on a mere portion of a U.S. penny. It is to be appreciated that the penny and the waveguide 2 in FIG. 1 are shown substantially to scale. Integrated photonic techniques can be used to miniaturize the total surface area encompassed by the waveguide 2 while also providing the waveguide 2 with an increased optical path length that is also highly confined, provides low propagation loss (i.e., "low-loss"), and is scalable. Furthermore, when the waveguide 2 is formed of $Si_3N_4$, the waveguide 2 is also capable of broadband light transmission.

To confine the waveguide 2 to the area shown in the illustrated embodiment, six (6) different constituent waveguides, each defined by a non-crossing, lithographically drawn field pattern, can be stitched together. In this example embodiment, the waveguide 2 is confined to a total field area of about 1 mm×6 mm, although other field sizes are possible. A magnified view of two of the constituent waveguides 2a, 2b is shown in dashed rectangle 4. A further magnified portion of one of the constituent waveguides 2b is shown in dashed rectangle 6. The waveguide 2 (and each of its constituent waveguides) can be defined by electron beam (e-beam) lithography, deep-ultra-violet (DUV) lithography, multi-pass lithography, a combination of the foregoing, or other types of nano-scale lithography. The waveguide 2 may have a rectangular cross-sectional geometry of, e.g., about 200 nm×350 nm, although other nano-scale cross-sectional geometries are possible. For example, segments of the waveguide 2 can have cross-sectional dimensions, such as width and/or height, each within a range from about 1 nm to about 1 μm, from about 1 μm to about 1 mm, or from about 1 mm to about 10 mm, and all intermediate values. It is also to be appreciated that the waveguides 68, 70 can have a total path length in the range from about 1 nm to about 10 m.

Referring now to FIG. 2, by integrating micro-heaters 8 with the waveguide 2, such as, for example, with each constituent waveguide, the waveguide 2 stability can be improved, while also providing the waveguide 2 with precise thermally controlled optical path tunability. $Si_3N_4$ is a preferred material for the waveguide 2 for a number of reasons, one reason being the favorable thermo-optic coefficient $\varepsilon$, as set forth above; another reason being that it can readily define bending radii of less than 50 μm, which allows the highly-confined, non-crossing field patterns also described above. Moreover, $Si_3N_4$ can transmit light having wavelengths from 250 nm to 6 μm, which enables broadband application. For example, a $Si_3N_4$ waveguide can transmit light at both 800 nm and 1 µm, which are both particularly useful in a number of various OCT applications.

Referring now to FIG. 3, to reduce propagation loss at stitch boundaries 10 between the different lithography fields 2a, 2b of the waveguide 2, segments 12 of the waveguide 2 adjacent the field boundary 10 may taper outwardly so as to be wider than segments 14 of the waveguide remote from the field boundary 10. Thus, the optical path is wider at the stitch boundaries 10 than at locations internal to the various fields. It was discovered that, even though the stitched boundary segments 12 of the waveguide 2 may be misaligned (which typically results from field shifts and stage instability inherent in most lithography processes, particularly those in the nano-scale), the tapered boundary segments 12 significantly decrease propagation losses across the stitch boundary 10. Without the adiabatic taper, a misalignment of even about 100 nm at the stitch boundary 10 may render the waveguide 2 virtually unusable. The foregoing adiabatically tapering method can in turn be employed via e-beam and DUV lithography to reduce propagation losses from stitching.

It has also been discovered that, according to simulations, the adiabatic taper region not only increases the transmission but also increases the tolerance of stitching. Using this and other low-loss fabrication methods, thermally tuned, low loss $Si_3N_4$ waveguides can be fabricated that are confined within a small area (e.g., 1 mm×8 mm or 1 mm×6 mm) yet define a comparatively long optical path length (e.g., of 42 cm or longer) all while exhibiting propagation losses as low as 0.27 dB/cm±0.04 dB/cm. The area and resultant optical path length can be scaled upward as desired, for example, to areas of 10 mm² or larger. The propagation loss can be further reduced using chemical-mechanical planarization and multipass lithography. Moreover, the thermo-optic coefficient ε of $Si_3N_4$ (about $2.45\pm0.09\times10^{-5}$ RIU/° C.) provides, as a non-limiting example, a 42 cm long waveguide optical path with tunability of about 21 µm per ° C. with sub-micrometer precision. Thus, by integrating the micro-heaters 8 with the $Si_3N_4$ waveguide 2, tunability in the centimeter scale can be provided. Micro-coolers for tuning the waveguide are also within the scope of the present disclosure.

It is to be appreciated that the dimensions of the waveguide 2, including the cross-section and optical path length, are highly scalable. For example, the optical path length is scalable from nanometer to meter ranges. This scalability allows the waveguide 2 to be tailored to meet the various requirements of different applications. It is also to be appreciated that the waveguide 2 can be formed of materials other than $Si_3N_4$. For example, the waveguide 2 or similar structures can be formed of SiN (a silicon nitride), silica (silicon dioxide—$SiO_2$) and/or silicon (Si). However, $SiO_2$ and Si present certain challenges. $SiO_2$ waveguides have been shown to barely exhibit a thermo-optical effect and thus lack the ability to be tuned, at least in any practical sense. Moreover, the absorption cutoff of Si occurs at 1 µm. Accordingly, for wavelengths less than 1 µm (which may be useful in many optical applications), another material, such as $Si_3N_4$ or SiN, may be preferable.

It is to be appreciated that nano-scale waveguides, such as those described above, can be utilized to improve numerous optical applications, including, OCT imaging and optogenetics, by way of non-limiting example. FIGS. 4 through 17 pertain to inventive OCT applications employing the waveguides of the present disclosure. FIGS. 18 through 37 pertain to inventive optogenetic applications employing the waveguides of the present disclosure.

Optical Coherence Tomography (OCT)

Referring to FIG. 4, an example embodiment of on-chip OCT imaging system 20 can include a thermally tunable waveguide 22 disposed on a substrate 24. The waveguide 22 can be configured similarly to the waveguide 2 described above with reference to FIGS. 1 through 3. In the present embodiment, the waveguide 22 includes two fields stitched together, although a single field or more than two fields are also suitable. The waveguide 22 is employed as the reference arm 26 of the OCT imaging system 20, which also includes a light source 27 in optical communication with a splitter 28 that is configured to direct a first portion of the emitted light to the reference arm 26 and a second portion of the light to a sampling arm 29.

The integrated on-chip $Si_3N_4$ reference arms described herein enhance the miniaturization of an OCT interferometer by providing a compact, low-loss, and tunable optical path. Thus, these waveguides not only improve the stability of the interferometric detection for on-chip OCT systems, it also allows significant reductions to the size and cost of the whole OCT system.

In SD-OCT systems, thermally tuning the reference arm simultaneously with A-line acquisition can allow any region of interest in an OCT image to be shifted into the high signal-to-noise ratio (SNR) regime of SD-OCT. In this manner, a sample image having high surface topology with high SNR can be obtained using SD-OCT by thermally tuning the reference arm. The full image can be reconstructed using automated stitching methods based on the path length changes produced in the reference arm. Such an implementation not only inherits the advantage of high resolution originally provided by SD-OCT, but also substantially reduces the amount of data generated during imaging. Notably, such an implementation of tunable waveguides renders SD-OCT feasible for high-resolution, high-topology imaging tasks.

Figure 5:
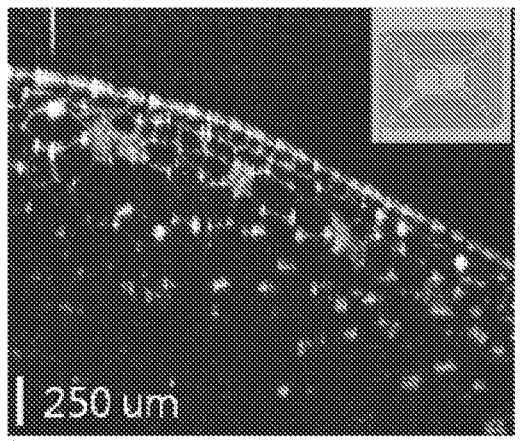
FIG. 5 is an image of an onion slice obtained with an existing (prior art) Spectral Domain, Optical Coherence Tomography (SD-OCT) imaging system.

FIG. 5 shows a B-scan of an onion obtained with a commercially available SD-OCT imaging system at 1300 nm. For comparison, FIG. 6 shows a B-scan of the same onion obtained with the a refurbished version of SD-OCT imaging system, wherein the stock fiber reference arm was replaced with an external, thermally tunable $Si_3N_4$ waveguide having a length of 3 cm.

Figure 6:
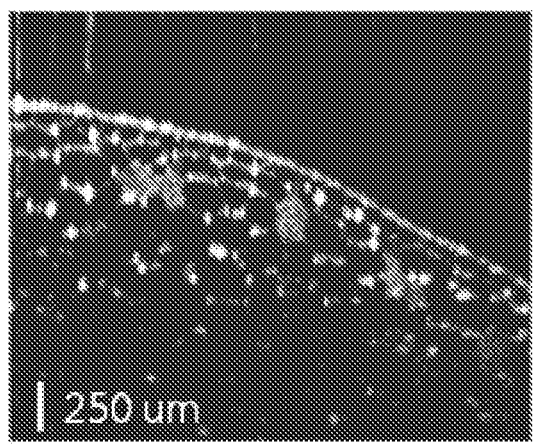
FIG. 6 is an image of the onion slice obtained with a refurbished SD-OCT imaging system employing a tunable waveguide as an external reference arm.
Figure 7:
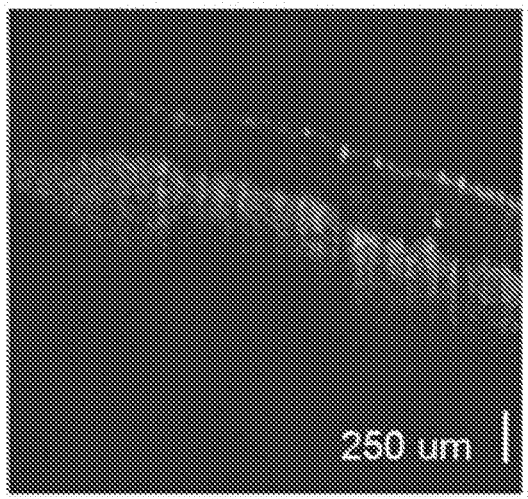
FIG. 7 is an image of a posterior view of a human finger obtained with the refurbished SD-OCT device used for FIG. 6.
Figure 8:
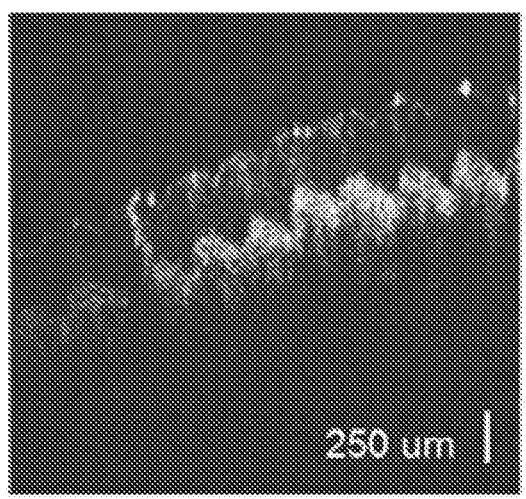
FIG. 8 is an image of an anterior view of the human finger obtained with the refurbished SD-OCT device used for FIGS. 6 and 7.
Figure 9:
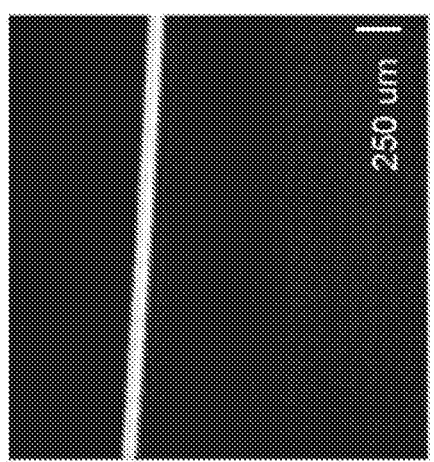
FIG. 9 is an image of a transverse view of a mirror surface obtained with the refurbished SD-OCT device used for FIGS. 6 through 8.

By comparing FIGS. 5 and 6, it can be seen that the image quality does not suffer despite using a miniaturized $Si_3N_4$ waveguide as an external reference arm. Although the dispersion compensation coefficients may need to be optimized after the insertion of $Si_3N_4$ waveguide, the impact on image quality is minimal. The refurbished SD-OCT imaging system was also used to image the back of a human finger, as shown in FIG. 7, the front of the finger, as shown in FIG. 8, and a mirror, as shown in FIG. 9. FIGS. 5 through 9 demonstrate that the waveguides disclosed herein can be used to replace the commonly used fiber or free-space based reference arms of current OCT imaging systems.

Figure 10:
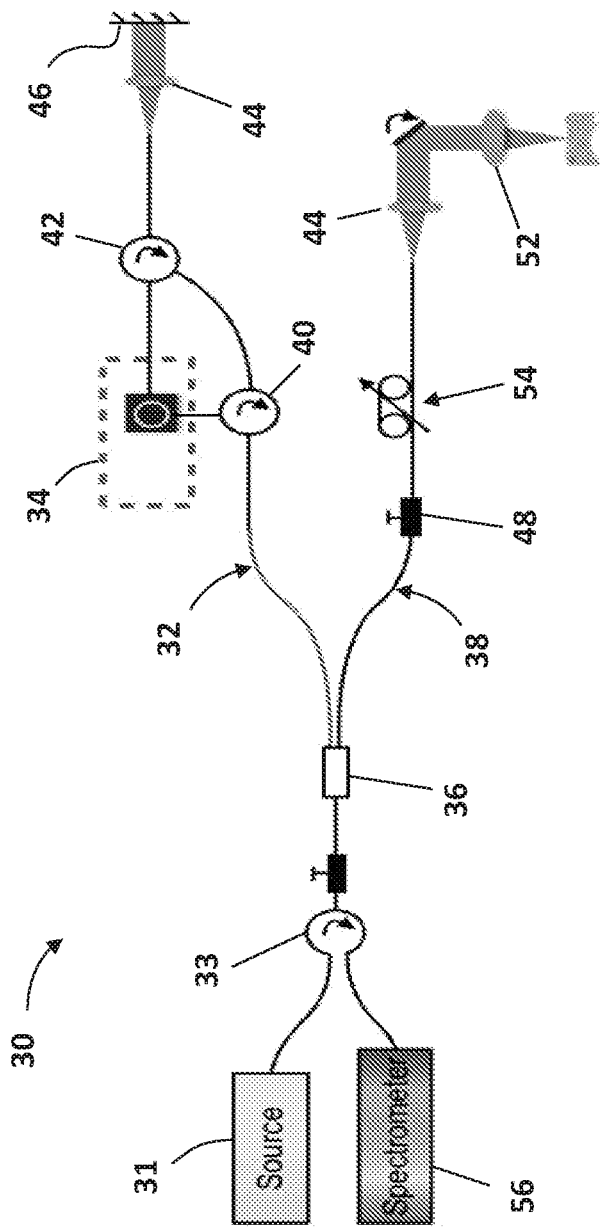
FIG. 10 is a schematic diagram of an example Spectral Domain Optical Coherence Tomography system that employs a thermally tunable waveguide as the system reference arm (according to an embodiment of the present disclosure)

Referring now to FIG. 10, to further test a tunable waveguide configured according to one example embodiment, a commercially available SD-OCT system 30 was refurbished so that its fiber reference arm was replaced with an external reference arm 32 employing a tunable waveguide, particularly an on-chip tunable $Si_3N_4$ waveguide 34 configured as described above. (The exemplary, non-limiting system 30 in this example was a Telesto Series I 1325 nm SD-OCT imaging system, produced by Thorlabs, Inc., based in Newton, New Jersey) The system 30 includes a light source 31 that directs light through a circulator 33 to a broadband fiber coupler 36 (also termed a "splitter") with a (exemplary) 75:25 split ratio to divide the input power into the sample arm 38 and the reference arm 32, respectively. In order to reduce the insertion loss of the waveguide chip, two circulators 40, 42 were added in the reference arm 32 to create a single path via the tunable reference arm 32. In the reference arm 32, the light emanating from the waveguide 34 was directed through a collimation lens 44 and reflected back to the circulators 40, 42 by a mirror 46 at the distal end of the reference arm 32.

Referring back to FIG. 2, the temperature tuning of the reference arm 34 in this example was realized by applying voltage to the heater electrodes (i.e., the micro-heaters 8) integrated on-chip and located on top of the waveguide 34. By applying voltage over the heater 8, it transduced electrical power to thermal power, heating the waveguide 34, and leading to the aforementioned changes in the refractive index and the optical path length of the reference arm 32. The temperature of the heater 8 was monitored through the voltage of a thermistor.

Referring again to FIG. 10, the sample arm 38 was controlled by a polarization controller 48 to optimize the image quality. Also in the sample arm 38, the light was transmitted through a collimation lens 50 to an x-y 2D scanner, which directed the light through a low-NA objective lens 52, which was adopted to ensure a long depth of focus (~2 mm in air), which is also necessary for high-topology imaging. As a result, the lateral resolution of the objective lens 52 was compromised to about 35 μm. In addition, an optical delay line 54 was inserted into the sample arm 38 for the path length matching. The OCT image quality was optimized carefully by controlling the polarization state of the sample arm 38 signal. In such a setup, the dispersion mismatch between the two arms 32, 38 can be fully compensated numerically during image reconstruction. Circulator 33 is also in optical communication with a spectrometer 56.

OCT raw data was acquired with commercial software, and cross-sectional OCT images and three-dimensional volumes were reconstructed following standard OCT data processing steps, including background subtraction, linear-k interpolation, apodization and dispersion compensation performed in MATLAB.

In this particular example, because 75% of the light source power was directed to the OCT interferometer, the sample arm power detected by the spectrometer was reduced by almost one-half due to the fiber splitter. This led to reduced signal penetration in OCT images. Without being bound to any particular theory, coupling loss at the external reference arm can lead to a relatively low SNR of the OCT image, limiting the imaging speed to 5.5 kHz A-line rate. Coupling stability (e.g., during temperature tuning) can include packaging, whereby micro-heaters can be integrated on-chip and pigtailed fibers utilized as output ports. One may also build the full reference arm on-chip and reduce the length of the sample arm to match the reference arm (see FIG. 4). Additionally, the micro-heater design, as well as a heat sink design, can be used to modulate heat transduction and dissipation.

It is to be appreciated that the images and data presented in FIGS. 11 through 17 were obtained with the refurbished SD-OCT imaging system 30 described above with reference to FIG. 10.

Figure 12:
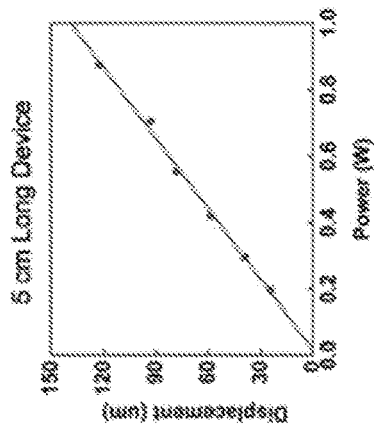
FIG. 12 is a graph showing the thermal behavior of a waveguide having a 5 cm optical path length.
Figure 11:
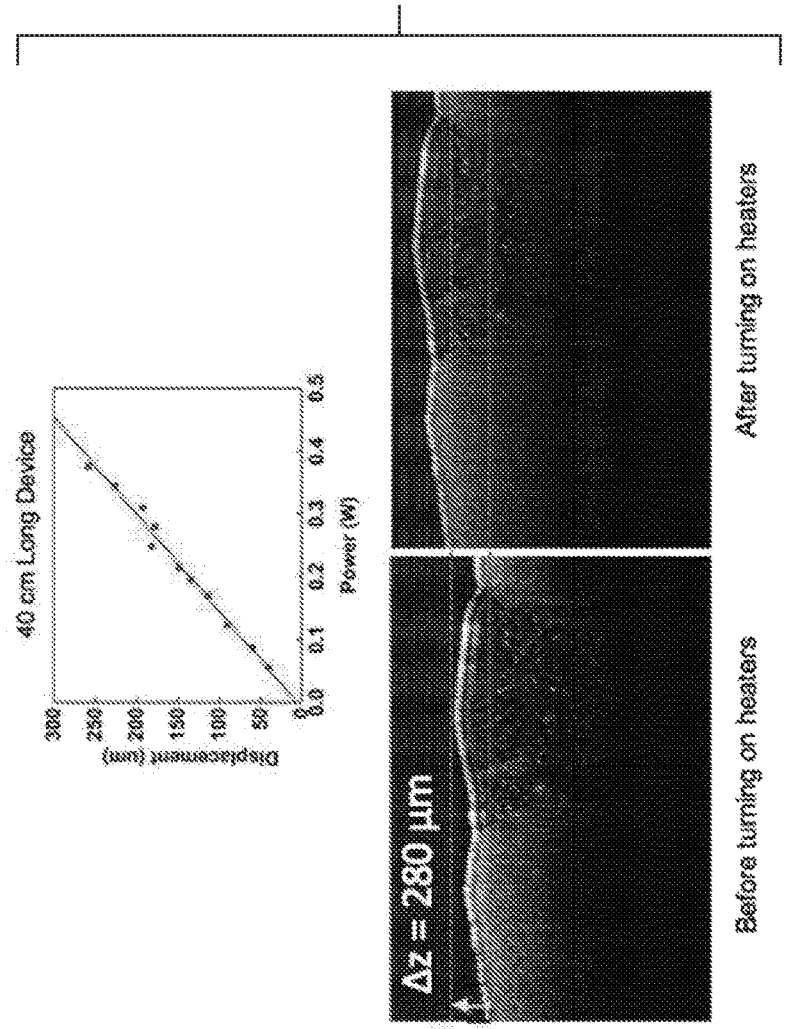
FIG. 11 illustrates a technique for measuring the thermal tenability of a waveguide having a 40 cm optical path length.

The thermal tunability of a reference arm employing the waveguides disclosed herein may be tested by placing a mirror in the focal plane of the sample arm. Referring now to FIG. 11, for different temperature settings, the displacement of the peak (at mirror location) can be recorded from the OCT image and plotted on a graph with the electrical power for heat generation on the x-axis and displacement on the y-axis. It can be seen that the displacement due to the change of refractive index is linearly correlated to the applied electrical power for heat generation. Specially, with a waveguide defining a 40-cm optical path length, a total single-path length change of 280 μm can be achieved without impacting the image quality. FIG. 12 shows a similar displacement versus power graph for a waveguide with a 5-cm optical path length.

Figure 13:
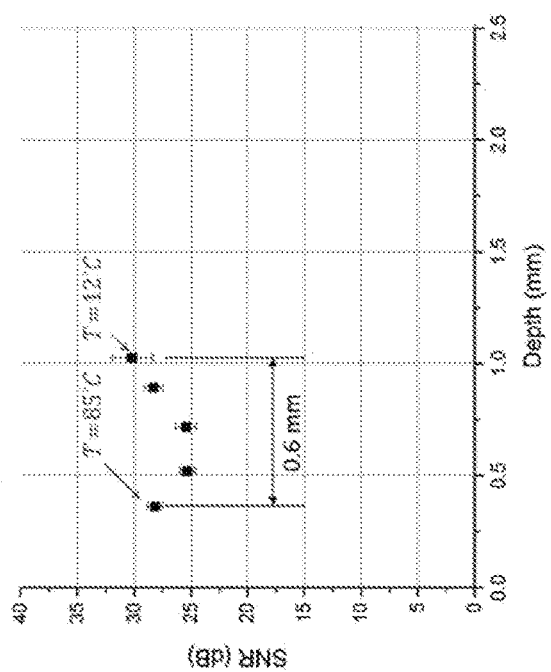
FIG. 13 is a graph showing the tuning stability of a waveguide, wherein the tuning stability is characterized by a change of signal-to-noise ratio (SNR) over the imaging depth as temperature changes.

Referring now to FIG. 13, the temperature tuning stability of the waveguide is demonstrated by measuring the SNR of the A-line signal for different temperature settings and plotting the change of SNR over the imaging depth as temperature changes. The change in temperature causes the refractive index of the waveguide to change and thus causes the image to shift. The temperature was tuned from 85° C. to 12° C. at 15° C. decrements. These changes resulted in a total image displacement of 0.6 mm with an increment of 0.15 mm. With a total temperature change of 70° C., the SNR maintains around 28 dB with a 2.5 dB standard deviation. The spectrometer 6-dB fall-off range is about 1.8 mm, which does not play a role in the tuning stability.

Figure 14:
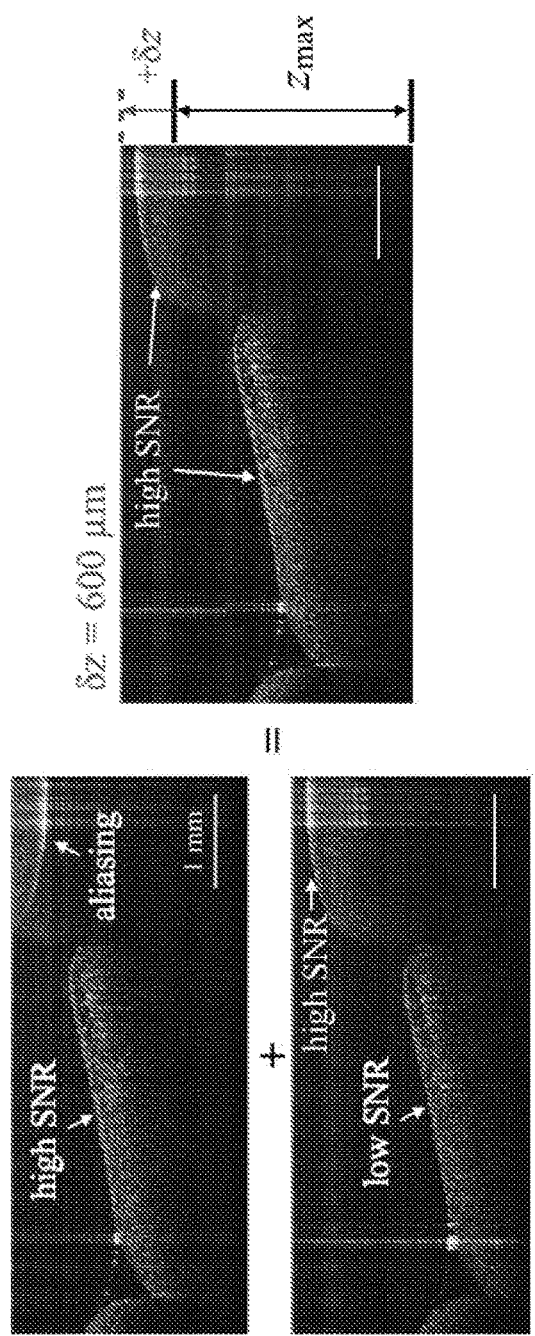
FIG. 14 shows OCT images taken at different waveguide input temperatures and stitched together to form a high-topology, high signal-to-noise ratio (SNR) image (made using the presently disclosed technology) of a human heart.
Figure 15:
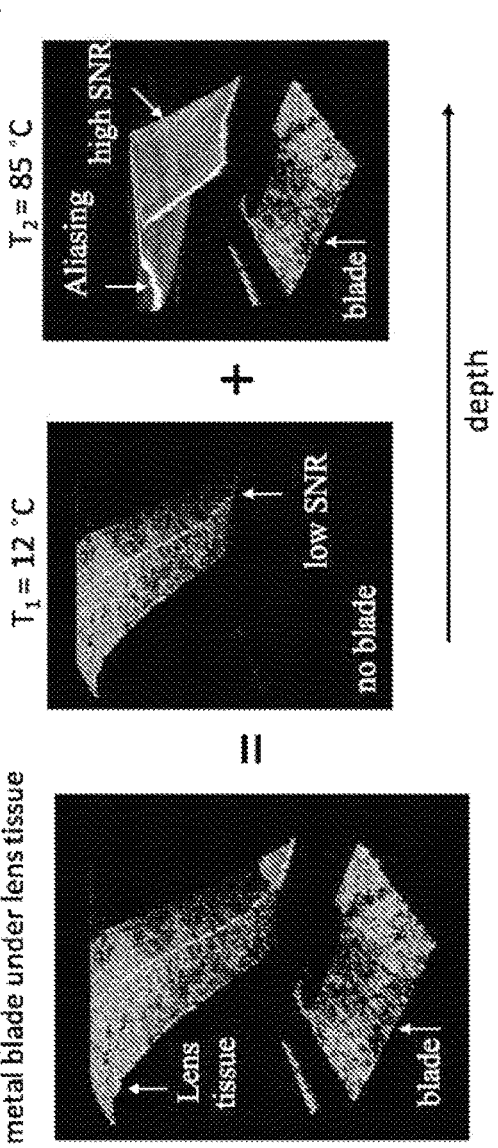
FIG. 15 shows a 3D, high-topology, high signal-to-noise ratio (SNR) stitched OCT image (made using the presently disclosed technology) revealing a blade otherwise hidden underneath tissue.

Referring now to FIGS. 14 and 15, high-topology, high-SNR OCT imaging is demonstrated with a tunable reference arm configured as described above.

In FIG. 14, a tissue wedge from the right ventricle of a fresh human heart was imaged. The OCT B-scans were taken from the endocardium side of the tissue, at two different temperatures. Because of the extra-long depth of focus of the low-NA objective, the sample arm surface across the field of view is in focus. However, the surface at the lower part of the OCT B-scan may have a reduced SNR, due to the fall-off of SD-OCT system. As illustrated in FIG. 14, a total displacement of around 600 μm is achieved by tuning the temperature from 12° C. to 85° C. The surface area with the lower profile can be brought up into the high SNR regime. By stitching the two B-scans together, a high-topology, high-SNR image is obtained.

FIG. 15 shows a 3D demonstration of high-topology, high-SNR imaging, where a metal razor blade is covered by lens tissue a novel imaging technique is used to unveil the razor blade. It can be seen that, with the reference arm is not tuned ($T_1$=12° C.), only the lens tissue is resolved by the SD-OCT system. The razor blade underneath the tissue is visible after thermal tuning has occurred (T2=85° C.). With 3D volume stitching, the full configuration is revealed. Similarly, FIG. 16 shows a 3D stitched OCT image of human skin covered by gauze, and FIG. 17 shows a 3D stitched OCT image of an aorta. It is to be appreciated that such high-topology, high signal-to-noise ratio (SNR) stitched OCT images have substantial value for industrial and other commercial applications in addition to medical applications.

Nanophotonics for Optogenetics

Tunable waveguides configured according to the present disclosure can also be employed in a first-in-class active silicon photonics device for visible light, enabling optical stimulation of neurons in arbitrary patterns at millisecond (μs) precision and to integrate it with an electrical probe that is implantable into the brain of a mammal. Current silicon probe technology enables large-scale recording of populations of single neurons but provides limited possibilities for optical stimulation of neurons. The active photonic devices described below provide the capability of optically stimulating arbitrary neural populations at millisecond precision and in deep regions of the brain, which otherwise remains a significant challenge in the field of optogenetics.

Figure 18:
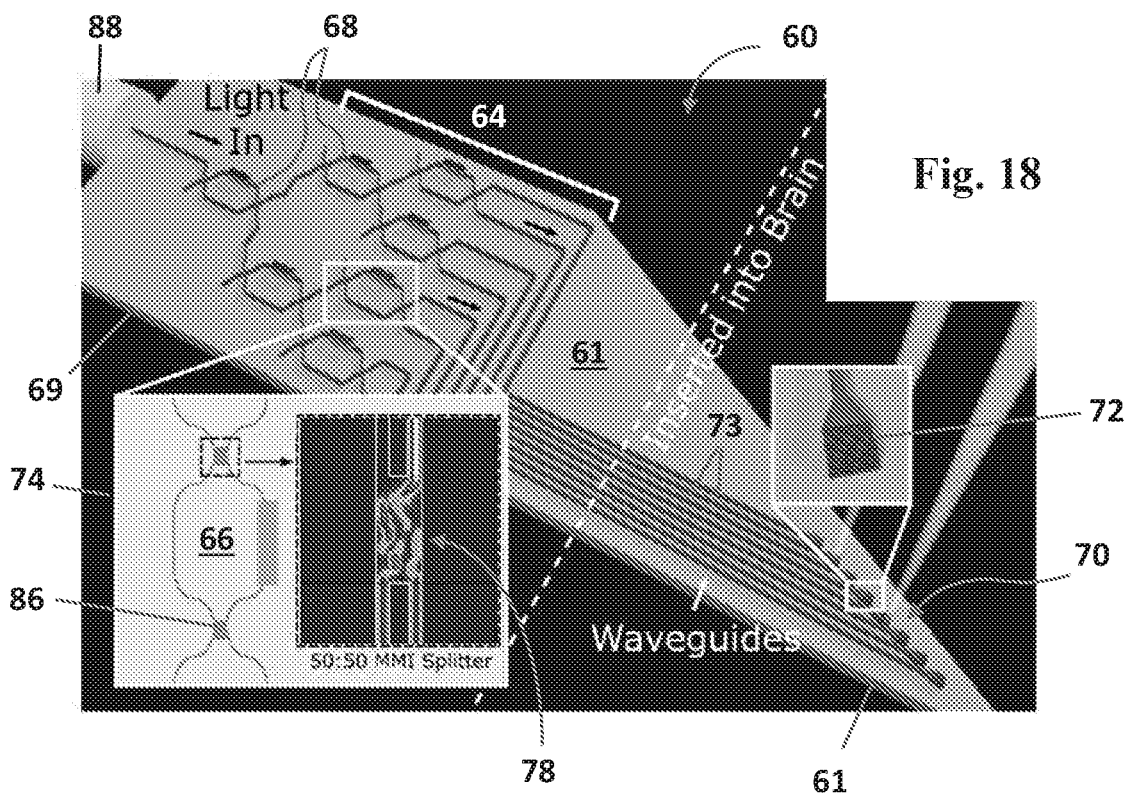
FIG. 18 shows a perspective view of an active nanophotonic device having a probe portion that is implantable for transmitting light within the brain of a living subject.

Referring now to FIG. 18, depicted is one example of an active nanophotonic device 60 for operation in the visible wavelength regime (400-600 nm—which regime is particularly relevant for optogenetics and most biological applications) to control a single beam or multiple independent beams for deep brain neural stimulation. The example device 60 includes a distal, probe portion 61 (also referred to herein as the "probe" or "shank") configured to be inserted into the brain and a proximal, external portion 62 configured to remain outside the brain. The external portion 62 supports, in one exemplary embodiment, a cascaded network 64 of 1×8 switches 66 employing thermally tunable silicon nitride waveguides 68 designed for transmitting blue light (λ=473 nm). These waveguides 68 in the switch network 64 can be characterized as "switching waveguides." An input fiber 88 can direct light from a single source, such as a laser, into the switching network 64. In other embodiments, multi-source configurations can be employed.

In some embodiments, the switching waveguides 68 can be formed of SiN wires that are about 0.2 µm in diameter and can be lithographically defined on a silicon (Si) substrate 69. Such waveguides 68 can be formed in a manner defining a highly efficient inverse taper, as more fully described in, e.g., NANOTAPER FOR COMPACT MODE CONVERSION (Almeida V R, Panepucci R R, Lipson M.), Opt. Lett. Optical Society of America; 2003 Aug. 1; 28(15):1302-4, the entire disclosure of which is incorporated herein by this reference for any and all purposes. Such waveguides 68 are transparent to light in the visible spectral range, like fibers, and can be made centimeters long. Compared to large fibers, these waveguides 68 are more than an order of magnitude smaller in diameter. Each waveguide 68 may be engineered so that light interacts very little with the environment, preserving its low-loss nature (typically about 0.1 dB/cm).

In other embodiments, the switching waveguides 68 can be formed of $Si_3N_4$ and can be configured similarly to those set forth above with reference to FIGS. 1 through 3. In such embodiments, the switching waveguides 68 can have a rectangular cross-sectional geometry of about 200 nm tall by about 350 nm wide, by way of a non-limiting example.

In the illustrated embodiment, a 1×8 (i.e., one input to eight outputs) optical switching network 64 is shown, although 1×16, 1×32, 1×64, 1×128, or >1×128 switching networks are also within the scope of the present disclosure. With continued reference to FIG. 18, the outputs of the switch network 64 are directed to an array 70 of eight (8) diffraction grating emitters 72 (i.e., emitters) disposed at a distal region of the probe portion 61. Each emitter 72 can be configured to emit a single beam of light perpendicular or oblique to the probe portion 61 for neural excitation. The array 70 of emitters 72 can be configured to direct light from the probe 61 into the brain, from any location along the probe 61. In the illustrated embodiment, diffraction grating emitters 72 are employed, which are corrugated structures with specific periodicity that causes light to destructively interfere at all directions except the out-of-plane direction. The geometry of each grating 72 can be designed to form a collimated output beam, for example, of about 20 µm diameter, for providing low diffraction and high neural excitation efficiency, while also providing single cell resolution. In particular, in some embodiments, individual gratings 72 can define a geometry of about 10 µm×0.5 µm, allowing an array of 128 gratings 72 (and thus 128 beams) to be aligned along less than 1 mm of probe length. It is to be appreciated that the density of gratings 72 that can be packed on the probe 61 may be limited only by the grating lengths. Moreover, unlike traditional metal mirrors, the gratings 72 have little or substantially no absorption.

The emitter array 70 can be densely packed, e.g., within a distance of 1 mm, and is preferably located at a distance (e.g., a few mm, such as about 4 mm) away from the switching network 64, which prevents undesired levels of heat dissipation and/or electrical interference within the brain, as described in more detail below.

The probe portion 61 can include additional waveguides 73 that communicate the network outputs to the emitters 72. These waveguides 73 can be characterized as "output" waveguides, and can be passive waveguides, although, in other embodiments, the output waveguides 73 can be active, thermally tunable waveguides for further manipulating the beam characteristics of light emitted from the array 70, as described in more detail below. It is to be appreciated that the switching waveguides 68 and output waveguides 73 can have cross-sections of various shapes, such as rectangular, circular, and elliptical, by way of non-limiting example. It is also to be appreciated that the waveguides 68, 73 can define cross-sectional dimensions, such as width and/or height, each within a range from about 1 nm to about 1 µm, from about 1 µm to about 1 mm, or from about 1 mm to about 10 mm, and all intermediate values. It is yet also to be appreciated that the waveguides 68, 70 can have a total path length in the range from about 1 nm to about 10 m.

With continued reference to FIG. 18, and as shown in a magnified view 74 of a switch 66 thereof, to create high extinction 1×2 switches 66 that are fast enough for neural applications, Mach-Zehnder interferometer (MZI) optical switches 66 are employed, which are based on fabrication tolerant splitters. At the input side of each switch 66, a first input arm 81 and a second input arm 82 are in optical communication with a splitter 78. The splitter 78 can employ a multimode interferometer (MMI) structure, which is more robust to small changes in fabricated dimensions, polarization, and wavelength than other types of splitters. Moreover, the splitter 78 can split the input light at a 50:50 (or other) ratio for equal distribution into a passive arm 83 and an active arm 85. Such an MMI-based splitter 78 is highly symmetric to achieve high extinction interference, as shown in the further magnified view 84 (which is a numerical simulation of the MMI Splitter within the MZI structure).

With continued reference to magnified view 74 of FIG. 18, the active arm 85 of each switch 66 can employ a thermally tunable, high-confinement, low-loss SiN waveguide 68 designed for blue light (473 nm). The waveguide 68 include integrated micro-heaters 84 for active, thermo-optic tuning in the manner described above. At the output side of the switch 66, the passive and active arms 83, 85 converge to an optically coupling 86, from which light from the passive and active arms 83, 85 are directed into a first output arm 88 and/or a second output arm 90 based on the interference characteristics in the coupling 86 (which is influenced by phase differences within the passive and active arms 83, 85).

Figure 19:
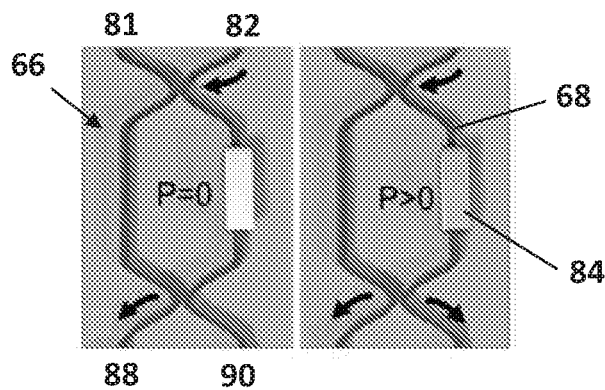
FIG. 19 is a schematic diagram of an active optical switch employed by the device of FIG. 18, showing the switch in OFF (left) and ON (right) configurations.

Referring now to FIG. 19, the switches 66 are operate by powering the respective micro-heaters 84 thereby inducing a small differential temperature profile on the waveguide 68, typically about 10-20° C., which in turn induces a phase change between the optical paths of the passive and active arms 83, 85. When the switch is ON, the optical paths constructively interfere, when OFF, the paths destructively interfere. Because the switches 66 operates on a differential temperature profile between the arms 80, 82, the switches 66 are relatively insensitive to ambient temperature fluctuations. Each of these switches has a fast time response of about 20 µs. By cascading n binary switches, light can be routed to $2^n$ emitters along the probe 61. Additionally, the thermo-optic coefficient ε of SiN (about $4\times10^{-5}$ K$^{-1}$) allows for efficient phase tuning at microsecond (μs) speeds, as set forth in more detail below.

Figure 20:
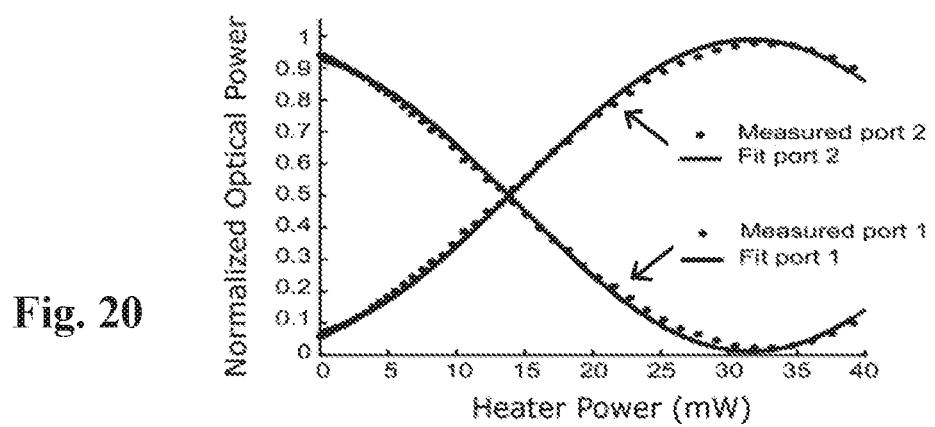
FIG. 20 is a graph showing normalized optical power of the output arms of the switch of FIG. 19 versus power delivered to a micro-heater integrated on an active arm of the switch.

Referring now to FIG. 20, each switch 66 can be optically characterized by measuring the light output from the gratings 72 as power is applied to the microheaters in different configurations. The graph plots the MZI output in the first and second output arms 88, 90 (as normalized optical power) as a function of heater power. From this graph, it can be extrapolated that the switches 66 demonstrate a 17 dB extinction ratio. The power consumption of the switches 66 is on the order of a few tens of mW, which can be reduced to less than 10 mW by designing the micro-heaters to overlap better with the waveguide mode. These switches 66 are capable of directing light between the first and second output arms 88, 90 at a switching speed of about 20 μsec.

Referring now to FIG. 21, the spatial distribution of the light output from the probe 61 can be imaged within a fluorescent dye (in this case, Alexa Fluor 488). Thus, as shown, arbitrary beam patterns with a beam divergence of about 3 degrees or less can be generated. However, other beam divergence angles can be achieved by tailoring the design of the diffraction gratings 72.

The SiN waveguide structures disclosed herein provides low loss and high confinement waveguides 64 in the visible wavelength range (starting from 400 nm) which allows reductions to the dimensions of the waveguides 64, as set forth above.

Fabrication of the device 60, according to one example fabrication process, can include the following exemplary steps: a 200 nm layer of low-pressure chemical vapor silicon nitride is deposited on a silicon substrate (wafer) with 5 μm of thermal oxide; then, the waveguide patterns are etched with e-beam lithography. The devices are then clad with 660 nm of high temperature oxide. Next, a metal lift-off process is used to pattern platinum heaters above the waveguides for thermal tuning. The devices are optionally diced at an angle so that the probe 61 tapers toward a pointed distal tip. The length of the probe portion 61 (i.e., the insertable length of the device 60) can be about 5.0 mm or greater, less than about 5.0 mm, less than about 2.0 mm, less than about 1.0 mm (1000 μm) (see FIG. 22), less than about 200 μm, and less than about 100 μm, for example. The silicon substrate is thinned to 250 μm using Bosch etching. For in vivo measurements, recording electrodes 87 may be present with (e.g., integrated with) one or more of the grating emitters 72 (alternatively, recording electrodes 87 can be disposed over (or otherwise in alignment with) the grating emitters 72, for example).

For electrode integration on the same substrate, a thin layer of metal (for example, 100 nm of platinum) can be deposited using a sputtering or electron beam evaporation process. This metal can be patterned using lift-off and electron beam lithography with dimensions on the order of about 20 μm in diameter. These dimensions are flexible depending on desired impedance for neural recording. The recording electrodes 87 allow the probe 61 to precisely record neural activity concurrent with neural stimulation.

It is to be appreciated that the external portion 62 of the device 60 can be wire-bonded to a printed circuit board (PCB) for controlling the switch network 64. The PCB can include, or otherwise be in electronic communication with, a control unit, such as a microprocessor, for example, that is configured to control operation of the device 60. In further embodiments, the optical components (e.g., the switch network 64 (including the switching waveguides 68 and the micro-heaters 84), the output waveguides 73 and the emitters 72) can be electronically coupled to a first PCB for controlling the optical components, and the neural recording components (e.g., the recording electrodes 87) can be electronically coupled to a second PCB for controlling operation of the recording components.

Device 60 can optionally include one or more support structures, such as lithographically patterned electrical circuit networks, for electronically coupling the optical components and the recording components to the first and second PCBs. It is to be appreciated that the device 60 can be configured for coupling with various commercially available devices and/or probes for recording neural activity. In such embodiments, the probe 61 can optionally be configured so that the emitters 72 and recording electrodes 87 are correspondingly aligned or otherwise positioned adjacent one another so that an electrode 87 records neural activity of a neuron activated by a corresponding emitter 70 or group of emitters 70.

Another example process for fabricating the device 60 can include the following steps: high temperature SiN deposition is performed on thermal oxide grown on a silicon wafer. The waveguides and reactive are patterned on the oxide layer via etching. Bosch etching is used to remove 450 μm of silicon from the backside of the probe, thinning the probe region to about 50 nm thick, while simultaneously removing the silicon from around the probe. The fabrication can be performed in a clean-room facility. The photonic structures, such as the waveguides, can be defined using deep-ultraviolet (DUV) lithography (in contrast to e-beam for example), in order to ensure a path for large-scale fabrication. The roughnesses of the photonic structures can reduced by using chemical vapor deposition (CVD) for the SiN films, combined with annealing and chemical mechanical polishing of the surfaces. Such processing techniques can decrease the average surface finish roughness of the waveguide surfaces to less than 1.0 nm (i.e., a few atoms). Such smoothness is helpful for minimizing the typically high scattering losses in these high-confinement waveguides, where light interacts strongly with all their interfaces especially in the blue spectral range, where losses scale as $1/\lambda^4$. The resulting SiN switching waveguides in the blue spectrum are almost two orders of magnitude smaller than currently available 1×16 commercially available MEMS-based switches for the visible spectrum. Furthermore, the waveguides processed as disclosed herein can be engineered to operate on a time scale of 1 μs for high confinement micro-sized devices. (It is to be appreciated, of course, that methods of fabricating the device 60 are not limited to the foregoing exemplary fabrication processes.)

Figure 24:
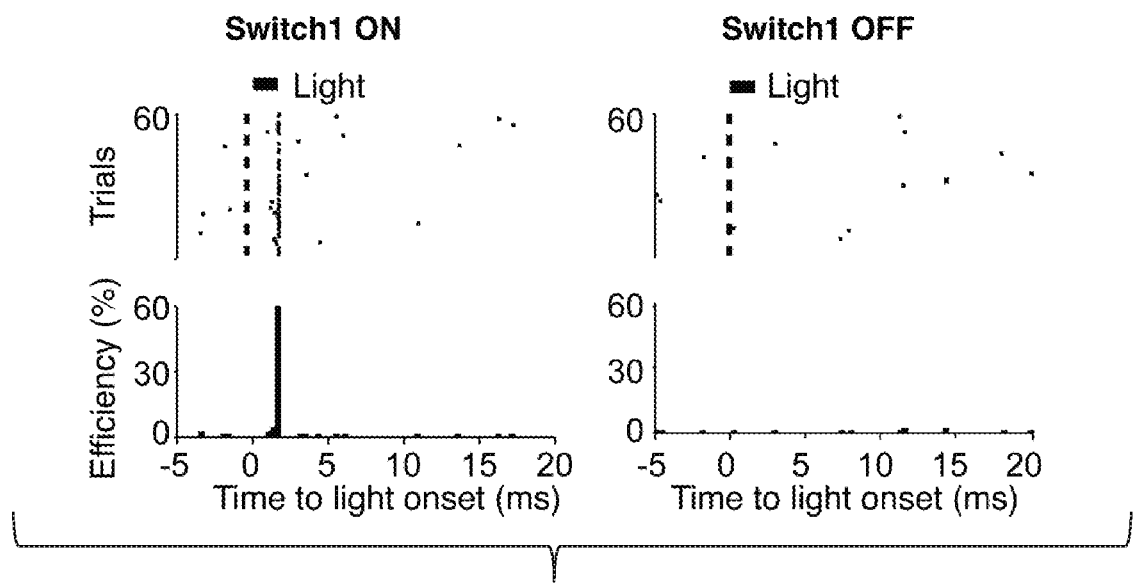
FIG. 24 shows a pen-stimulus time histogram showing precisely timed action potentials generated by the stimulated neuron with light pulses from the probe.

FIGS. 23 and 24 show results of a first test of neural stimulation with an active nanophotonic device. In this test, a probe having a 1×4 switching network (and otherwise configured similarly to the probe 61 shown in FIG. 18) was used. The probe was tested in anaesthetized transgenic mice crossed with Ai32 ChR2-YFP reporter mice. In these mouse lines, a population of PV inhibitory neurons expresses the light-sensitive ion channel, ChR2. It was found that the probe could be readily inserted and lowered into the visual cortex without excessive tissue damage thereto or damage to the probe. The optical probe was aligned with a tungsten electrode array (1 MΩ, 1 μm tip, World Precision Instruments) using optical adhesive. PV-Cre (inhibitory neurons) in the visual cortex were targeted with beams emitted from the probe in 1 ms light pulses. Neuron activation was recorded with the tungsten electrode array. As shown in FIG. 23, the light-evoked neural spike waveform is virtually identical to a spontaneous neural spike waveform. As shown in FIG. 24, alignment to the 1 ms light pulse revealed low latency and low jitter spikes. It was also found that increasing light intensity above the threshold did not yield additional spikes due to secondary activation by other neurons, indicating that the device can activate multiple individual neurons independently, which, to the inventors knowledge, has not been demonstrated with conventional optical fibers. Additionally, increasing the light levels also increased the probability of a neural spike, while the first spike jitter remained the same. Based on the low latency and jitter of responses and because inhibitory neurons were targeted, the responses were from directly activated neurons.

Figure 25:
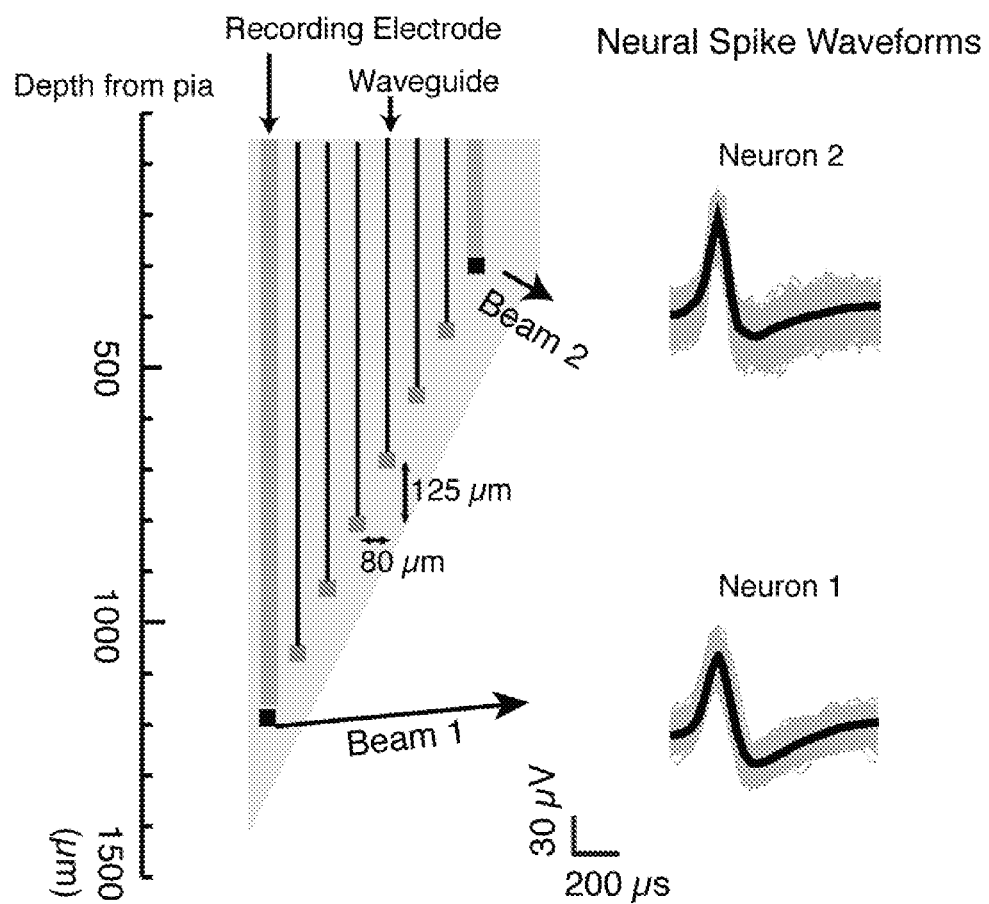
FIG. 25 is a schematic of the probe showing exemplary alignment of recording electrodes with optical beams, as well as voltage waveforms recorded from stimulated neurons.
Figure 26:
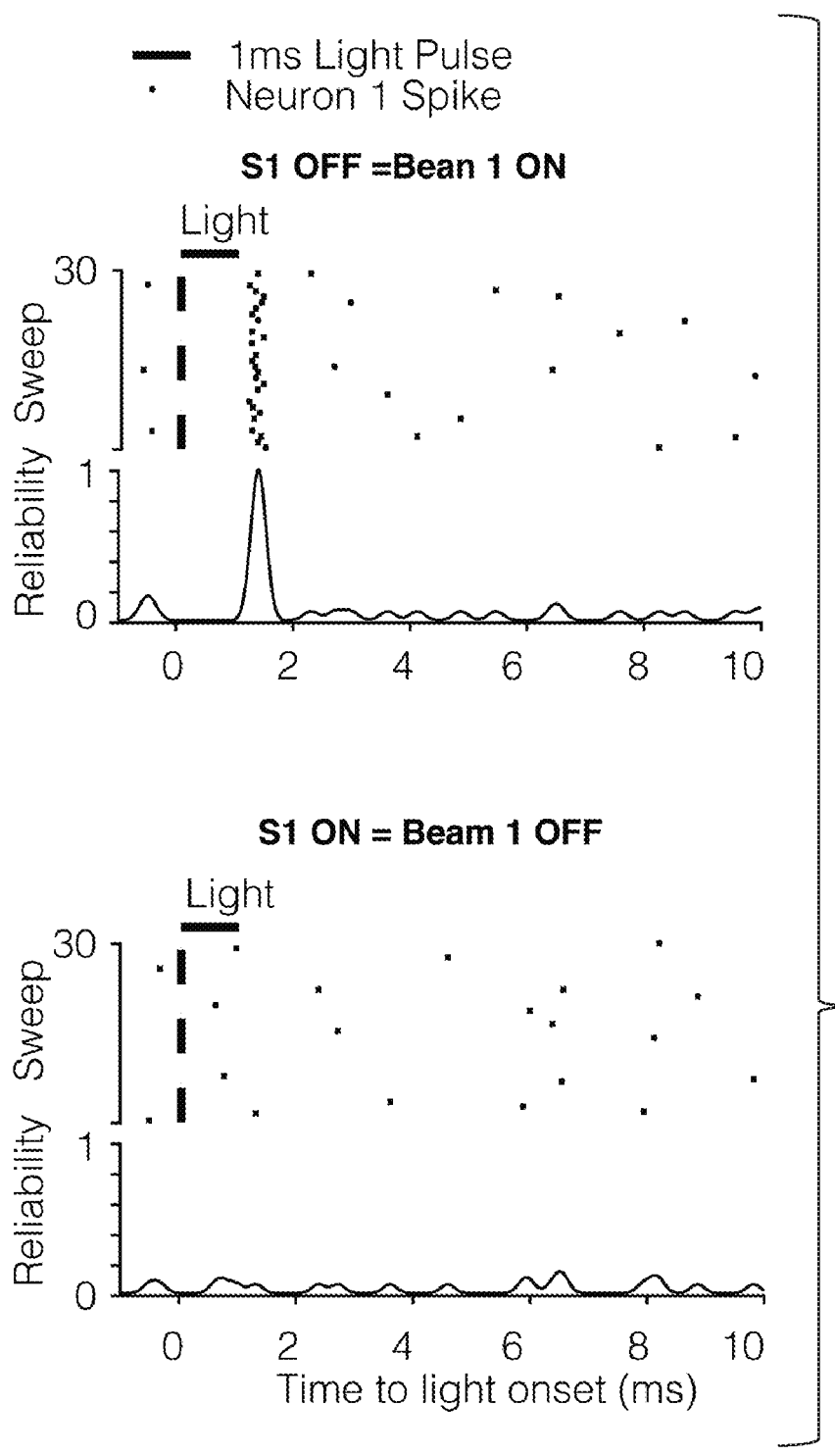
FIG. 26 is an example pen-stimulus time histogram showing precisely timed action potentials (dots) generated by a stimulated neuron with light pulses from a beam (heavy lines) responsive to switching the lead switch in the network shown in FIG. 18.
Figure 27:
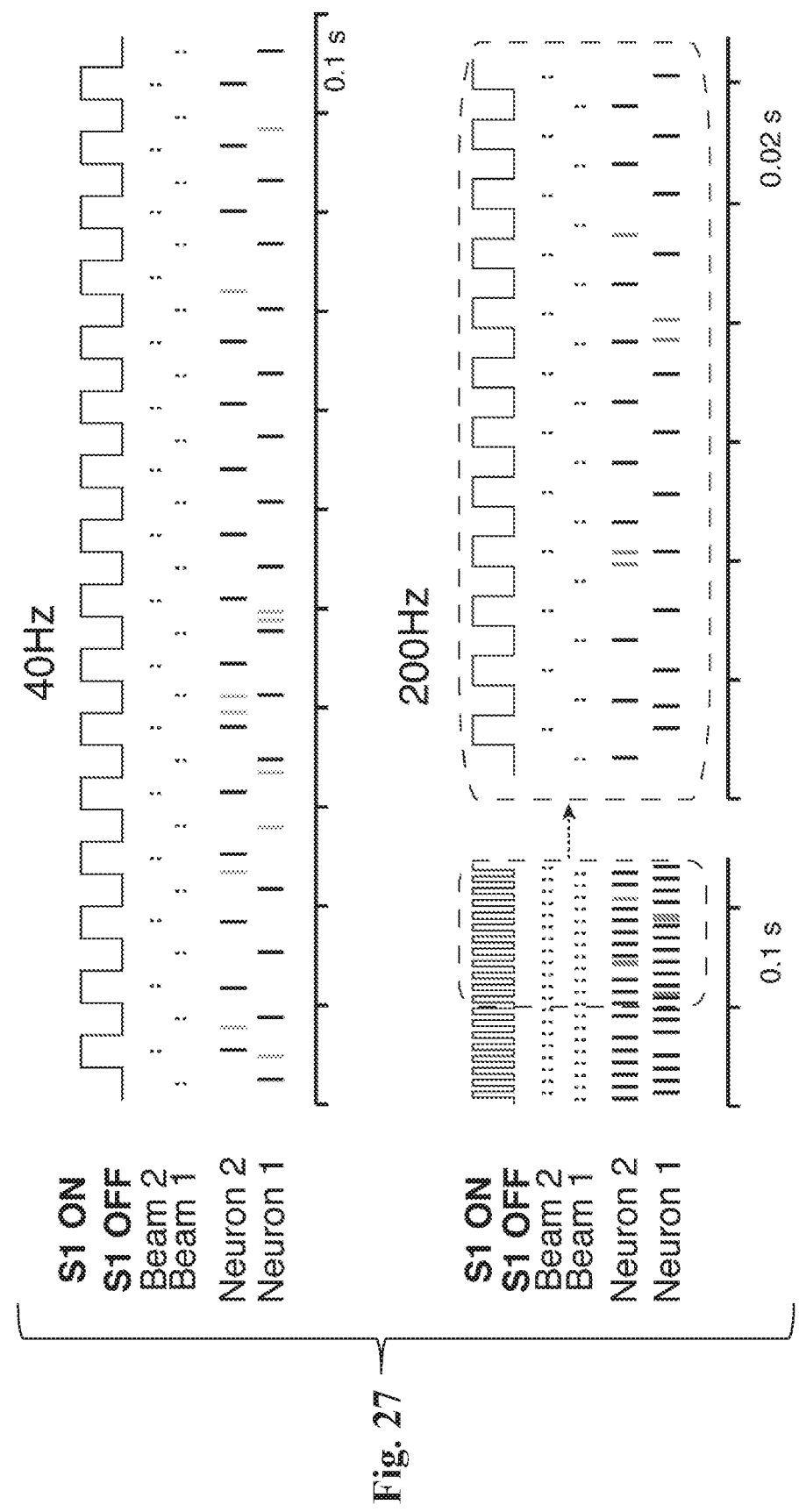
FIG. 27 shows charts plotting switch configurations (top, square waveform), generated optical beam signals (blue line), and recorded neuron signals (green and purple dots) at 40 Hz (top chart) and 200 Hz (bottom chart). When S1 (the lead switch)=ON, beam 2 emits. When S1=OFF, beam 1 emits.

FIGS. 25 through 27 show results of a second test of neural stimulation with an active nanophotonic device. In this test, the probe 61 of FIG. 18 (with a 1×8 switch network) was tested in the visual cortex of a mouse to demonstrate the probe's neural stimulation and recording capabilities. Virus delivery of ChR2 or ChETA opsins to target inhibitory interneurons in the mouse to demonstrate high-frequency stimulation. As shown in FIG. 25, the probe 61 included a pair of recording electrodes 87 aligned with the outer-most emitters 72 (and thus the optical beams emitted therefrom). The recording electrodes 87 detected voltage changes triggered by the stimulation of single neurons by Beam 1 and Beam 2, respectively through sixty (60) trials, each measuring the timing of the electrical neural spikes relative to the optical pulse. As 1 ms light pulses are delivered and power is applied to switch 1 in the switch network at 40 Hz and 200 Hz, the light is routed from Beam 1 to Beam 2 (see FIG. 27). FIG. 26 is a pen-stimulus time histogram showing that the neurons follow the switch configuration with high efficiency. A high correlation can be observed between electrical spikes generated from the stimulated neuron 1 (black) with light pulses from Beam 1 (blue) following configuration of the lead switch of the switching network. Robust spike firing with 1.5 ms spike latency and 0.5 ms spike jitter are also demonstrated, which are typical for optogenetic experiments. The correlation between the light-evoked and spontaneous spike waveform for both neurons is calculated to be about 97%, which demonstrates that the probe 61 is not measuring a light-induced artifact. Thus, the probe 61 enables the generation of robust and repeatable stimulation patterns of single neurons in the visual cortex by correlating the optical signal for stimulating the cells with the electrical signal generated from the cells.

The foregoing experiments demonstrate that, using active switching on a nanophotonic platform, patterns of single neurons can be generated at unprecedented frequencies by an implantable probe with high timing precision (e.g., <1 ms), which may be important for understanding behavior in animals. It is to be appreciated that the design of the device 60 allows for scaling the number of controllable emitters 72 and recording electrodes 87 upward, which can allow large-scale studies of neural activity with high precision in behaving animals.

Figure 28:
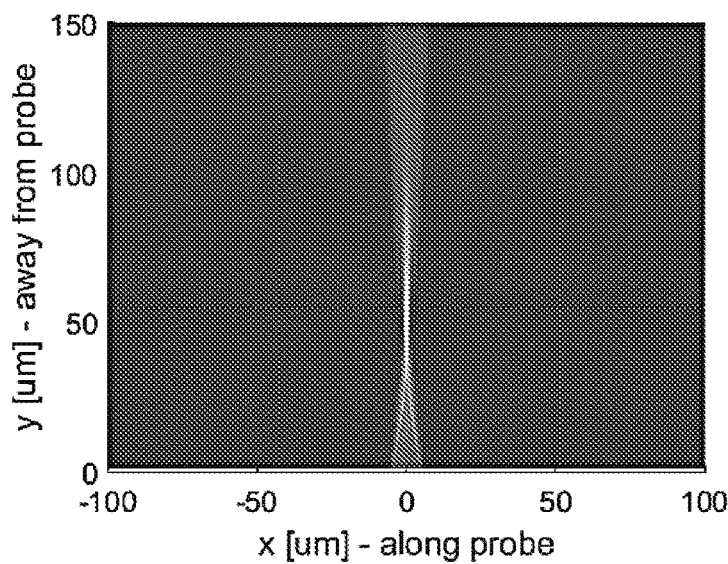
FIG. 28 shows a simulated focused beam produced by a phased array of emitters along a probe.
Figure 29:
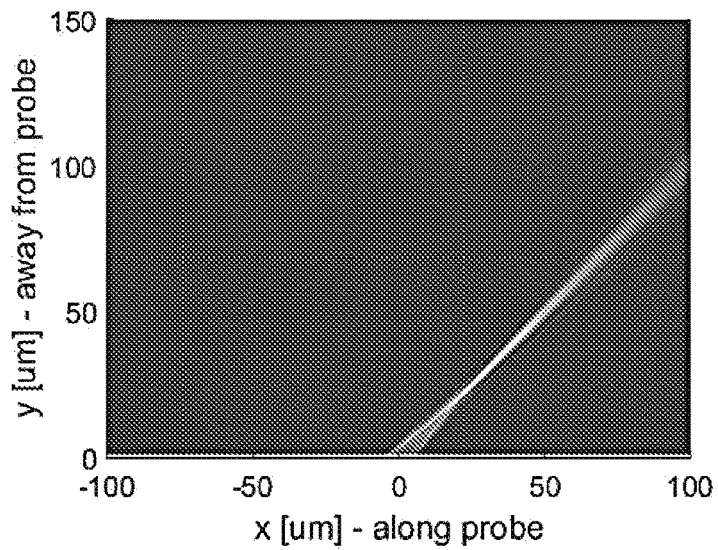
FIG. 29 shows a simulated focused and angled (steered) beam produced by a phased array of emitters along a probe.
Figure 30:
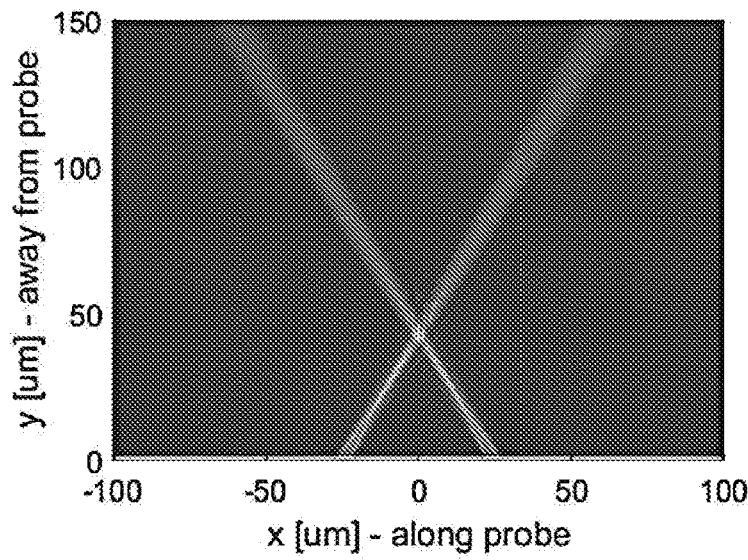
FIG. 30 shows a simulated pair of angled beams produced by a phased array of emitters along a probe.

The switch network 64 can also be employed to manipulate the light emitted by the emitter array 70. For example, the emitter array 70 can be employed as a phased array for shaping wavefronts within the emitted light (i.e., wavefront engineering). FIGS. 28 through 30 show simulated beams produced by emitters 72 in a phased array in the blue spectral range. In embodiments where the emitters 72 are densely spaced so that adjacent emitters 72 are located within one wavelength of each other, the switching network 64 can be controlled so that the light emitted by the array 70 constructively interferes in a manner producing a single beam (FIGS. 28 and 29) or multiple beams (FIG. 30). By actively modulating the phases within the switching network 64 (via thermally tuning the waveguides 68), the emitters 72 can be "phase ramped" or otherwise influenced to tune (i.e., steer) the beam to different angles, as shown in FIGS. 29 and 30. Such angle tuning can be accomplished with linear phase ramps, for example. Additionally, the emitters 72 can be phase ramped to focus the beam at a particular distance from the probe 61, as shown in FIGS. 28 and 29. Such beam focusing can be accomplished with quadratic phase ramps, for example. By steering and focusing the beam, individual neurons can be targeted. Moreover, by phase ramping smaller subsets of emitters 72 in the array 70, multiple tunable beams (FIG. 30) or other beam patterns can be created, steered, and focused, which can be used to create arbitrary patterns. For blue light (473 nm), such a phased array may require >32 output waveguides with half to full wavelength spacing for the emitters 72. Beam tuning can also be carried out via amplitude control. It is to be appreciated that active beam manipulation can be carried out periodically or continuously.

It is to be appreciated that, in other embodiments, in lieu of the switching network 64 described above, the device 60 direct a plurality of light sources to an array of respective output waveguides 73 that terminate at diffraction grating emitters 72. In such embodiments, phase modulators (lacking MZI or other interferometer) can be fabricated on each of the waveguides 73 for active wavefront shaping (i.e., both amplitude and phase control) to steer and focus a single beam (as in FIGS. 28 and 29), as well as to compensate for scattering effects of the target medium (i.e., brain matter). Preferably, the phase modulators include heaters, such as stand-alone micro-heaters, although other modulator structures are within the scope of the present disclosure.

In further embodiments, a combination of active, networked switches and output waveguides 73 can be employed to provide multiple phased arrays. For example, with reference to the device of FIG. 18, alternatively, individual output arms 88, 90 of the switches 66 can each be in optical communication with a respective phased array, for example, a phased array of output waveguides 73 and diffraction grating emitters 72. It is to be appreciated that other combinations of switching waveguides 68 and output waveguides 73 and emitters 72 can be employed for further tailoring beam output.

Figure 31:
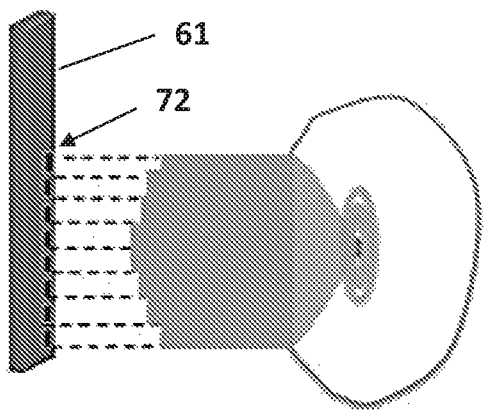
FIG. 31 shows a diagram of wavefront shaping.
Figure 32:
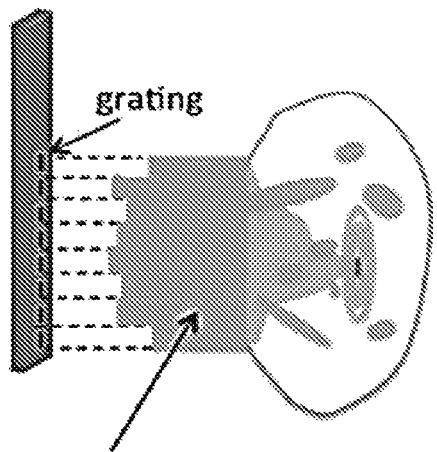
FIG. 32 shows a diagram of wavefront shaping involving pre-compensating for scattering effects in the medium.

Referring now to FIGS. 31 and 32, phased arrays can be utilized for engineering wavefronts that are tailored for the imaging medium, in this case, brain matter. As shown in FIG. 31, the emitter array 70 can be controlled to provide a waveform tailored to focus within a low scattering portion of brain tissue. Additionally, as shown in FIG. 32, the incident wavefront can be appropriately shaped (i.e., pre-compensated) so that the light can be focused even deep inside the most strongly scattering materials. It is to be appreciated that pre-compensation and steering can be utilized together to focus the light from the emitters 72 onto individual neurons. The active waveguide platform offers sub-msec time resolution and is thus an improvement over other techniques for shaping wavefronts in scattering tissue, such as spatial light modulator (SLM) techniques, which are significantly slower. The phased array wavefront engineering can be enhanced by using genetic algorithms that use feedback from the recording electrodes 87.

Figure 33:
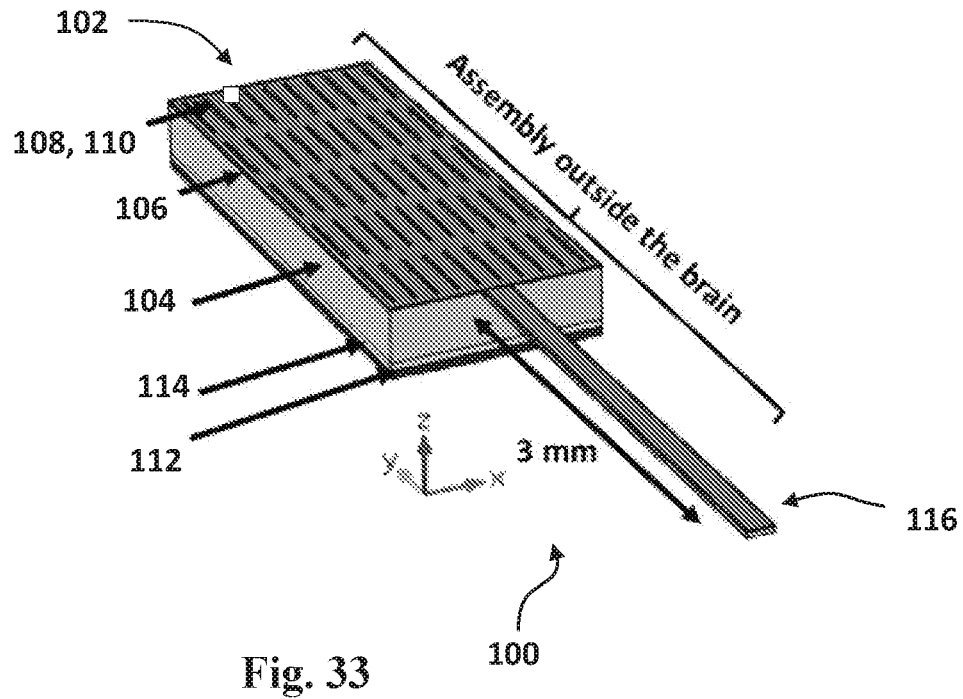
FIG. 33 is a 3D model used for simulating the heat distribution properties of the active nanophotonic device of FIG. 18.

Referring now to FIGS. 33 through 37, simulated test results of a model 100 of the device 60 will now be discussed. As mentioned above, the device 60 is designed to ensure that the heat in the assembly outside the brain is dissipated extremely fast, within tens of microns from the heaters, resulting in an insignificant change in the overall temperature of the implanted probe 61. As shown in FIG. 33, the simulated model 100 includes a proximal (external) portion 102 that comprises a silicon substrate 104 that supports an oxide ($SiO_2$) layer 106 having SiN waveguides 108 defined thereon. Platinum micro-heaters 110 are formed over the waveguides 108. A copper heat sink 112 is coupled to the bottom of the substrate 104 with a high-conductivity thermal paste 114, in particular a silver sintering paste. A probe 116 extends from the external portion 102 in the y direction.

The dominant path of heat from each micro-heater 110 is through the silicon substrate 104 to the copper heat sink 112. The temperature profile of the model 100 was simulated using a Finite Element Method, taking into account the heat conduction through the solid components including the probe 116, the conductive paste 114, and the copper heat sink 112. Moreover, the model 100 considers the thermal conductivity and geometry of its constituent components.

Figure 34:
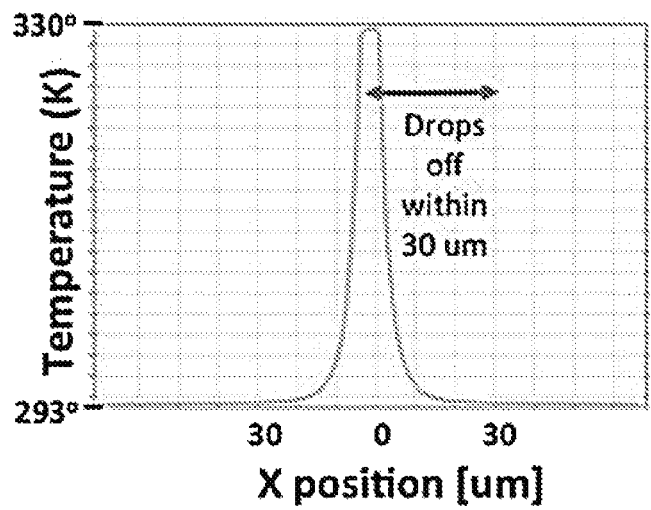
FIG. 34 is a graph showing a simulated temperature distribution of the model (of FIG. 33) along the x direction.
Figure 35:
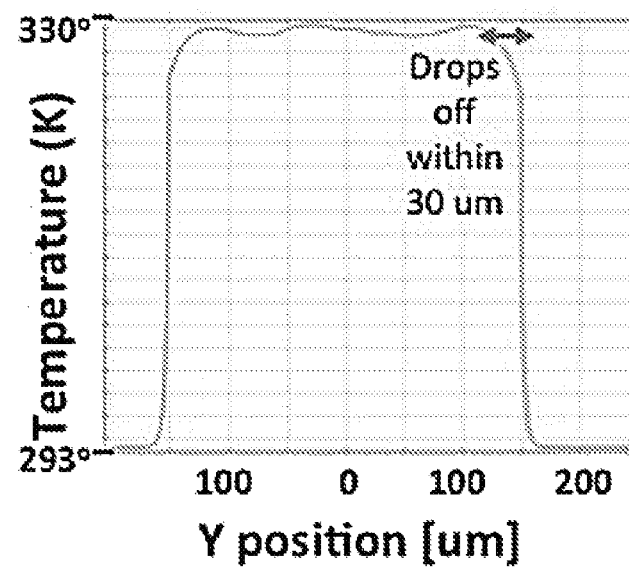
FIG. 35 is a graph showing a simulated temperature distribution of the model (of FIG. 33) along they direction.
Figure 36:
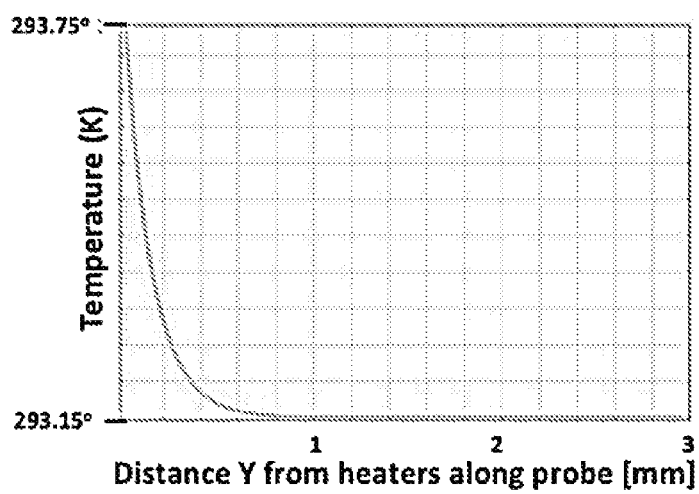
FIG. 36 is a graph showing a simulated temperature distribution along a probe portion of the model (of FIG. 33) along they direction.
Figure 37:
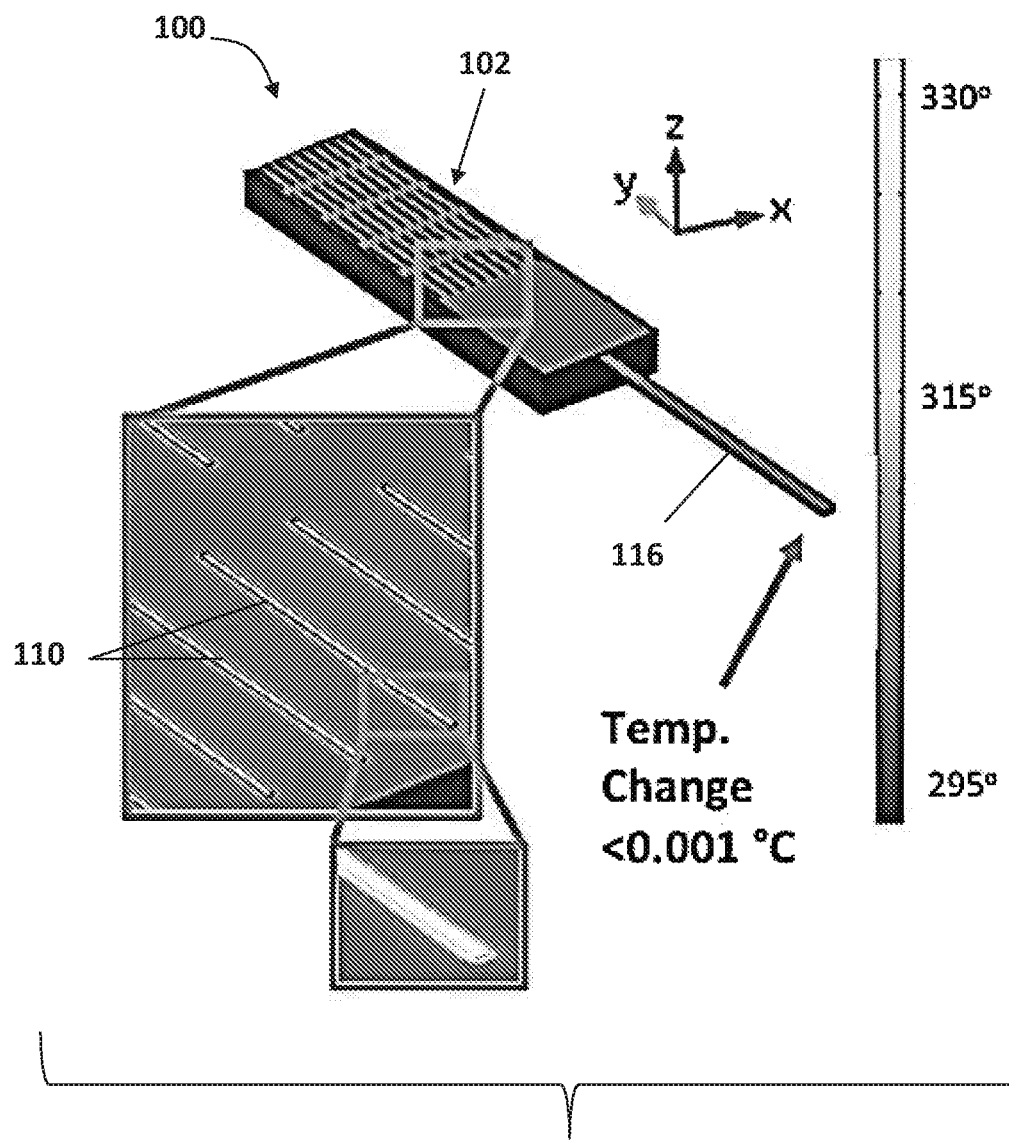
FIG. 37 shows a simulated temperature distribution on the 3D model (of FIG. 33) itself.

FIGS. 34 and 35 show that the temperature drops to room temperature within 30 μm of the peripheral edges of the external portion 102 in both x and y directions. This strong temperature profile allows the creation of compact (and therefore fast) devices 60. It also ensures that the temperature at the distal tip of the probe 61 does not change significantly due to the micro-heaters (see FIG. 36). In order to ensure that the temperature increase at the distal tip of the implanted probe 61 remains minimal even as the number of micro-heaters 84 increases, optical circuitry was designed, including the switch network 64, to ensure that the external area of the chip increases proportionally. FIG. 37 show that when fifty (50) micro-heaters 110 are modeled, even when assuming an extreme case where all of them are ON at the same time with a 50% duty cycle, a temperature change at the tip of the probe of less than 0.001° C. is induced.

In some embodiments, the device 60 is configured so that the probe 61 has a maximum temperature (during use) that is no more than 2° C., and preferably less than 1° C., above the normal brain temperature of the implanted subject.

It is to be appreciated that the external portion 62 of the device 60 can be made as large or as long as necessary for particular applications. Furthermore, the external portion 62 need not be limited to a chip or chip-like structure. For example, the external portion 62 can be a dermal patch, a cap-like structure that can be fitted to or otherwise worn on the head of the test subject, or virtually any other type of external structure carrying circuitry for operating the device 60. The external portion 62 can also be configured to be operated remotely, for example.

It is also to be appreciated that the device 60 can be employed to transmit wavelengths of light are effective to suppress, reduce, or eliminate stimulation of neurons.

It is yet also to be appreciated that the device 60 can be tailored to effectively operate in "reverse" to the techniques described above. For example, in such an embodiment, the neurons can be exposed to chemistry or the like that causes the neurons to illuminate when stimulated. The optical paths of the device 60 could be deposited in reverse, with photonic structures for collecting the neural illumination on the probe, which can be in optical communication with emitters on the external portion for emitting the collected neural illumination onto on optical sensor, such as a CMOS sensor, by way of non-limiting example. In additional embodiments, the probe 61 can be used to detect neural activity from genetically encoded voltage sensors, calcium sensors, or chemical sensors or the like. In further embodiments, the probe 61 can be configured for intrinsic imaging of neural activity.

Additional example embodiments of the present disclosure are set forth below.

Embodiment 1: A device, comprising: a distal portion configured to be implanted in a brain of a subject, the distal portion comprising one or more emitters configured to emit light in the visible spectrum; and a proximal portion configured to be external to the brain of the subject while the distal portion is implanted, wherein the proximal portion includes at least one waveguide in optical communication with the one or more emitters, the at least one waveguide defining a cross-sectional width less than 500 nm, wherein the at least one waveguide is optionally coupled to a heating element that is optionally configured to adjust a phase of light within the at least one waveguide.

Embodiment 2: The device of Embodiment 1, wherein the at least one waveguide consists essentially of silicon nitride.

Embodiment 3: The device of Embodiment 1 or Embodiment 2, wherein the at least one waveguide comprises silicon nitride.

Embodiment 4: The device of any one of Embodiments 1-3, wherein the at least one waveguide comprises $Si_3N_4$ and optionally has a polygonal (e.g., rectangular) cross-sectional geometry. The waveguide may have dimensions of, e.g., 200 nm tall by about 350 nm wide.

Embodiment 5: The device of any one of Embodiments 1-3, wherein the at least one waveguide is a SiN wire, the wire optionally having a diameter of about 0.2 μm.

Embodiment 6: The device of any one of Embodiments 1-5, wherein the at least one waveguide defines an optical path length of at least about 10 cm. The waveguide may define an optical path length of 2, 3, 4, 5, 6, 7, 8, 9, 10, 11, 12, 13, 14, 15, 16, 17, 18, 19, 20, 21, 22, 24, 25 cm, or greater, including all intermediate ranges and values.

Embodiment 7: The device of any one of Embodiments 1-6, wherein the proximal portion comprises a silicon substrate supporting an oxide layer. Optionally, the at least one waveguide may be patterned on the oxide layer, e.g., via e-beam lithography or DUV lithography.

Embodiment 8: The device of Embodiment 7, further comprising a heat sink coupled to the substrate.

Embodiment 9: The device of any one of Embodiments 1-8, wherein the proximal portion carries an optical switch having an input arm, a first output arm, and a second output arm, wherein the at least one waveguide defines at least a portion of the optical switch, and wherein the at least one waveguide is configured to direct light, responsive to the phase, into the first output arm, into the second output arm, or into both the first and second output arms.

Embodiment 10: The device of Embodiment 9, wherein the optical switch is an interferometer, and the waveguide defines a reference arm of the interferometer.

Embodiment 11: The device of Embodiment 9 or 10, wherein the optical switch is characterized as a Mach-Zehnder interferometer.

Embodiment 12: The device of Embodiment 10 or 11, wherein the optical switch comprises a cascaded network of optical switches that include a lead switch, in which network each optical switch except the lead optical switch has an input arm defined by an output arm of another one of the optical switches in the network, each optical switch in the network has first and second output arms that are each in optical communication with the one or more emitters, each optical switch is an interferometer having a reference arm defined by a waveguide, and each waveguide is coupled to a respective heating element configured to adjust the phase of the respective waveguide.

As explained elsewhere herein, a device may include one or more heat sources. A heat source may be used to modulate a component of a device, e.g., an optical switch and/or a waveguide, as explained elsewhere herein.

Embodiment 13: The device of Embodiment 12, wherein the network is a 1×4, 1×8, 1×16, 1×32, 1×64, 1×128, or a>1×128 network of optical switches.

Embodiment 14: The device of Embodiment 12 or 13, further comprising a source for the light, the source configured to transmit the light into the input arm of the leading optical switch, wherein the light is optionally blue light having a wavelength of about 473 nm.

Embodiment 15: The device of any one of Embodiments 12-14, wherein each optical switch is configured to direct the light between the respective first and second output arms at a switching speed faster than about 1 ms.

Embodiment 16: The device of Embodiment 15, wherein the switching speed is about 20° s or faster.

Embodiment 17: The device of any one of Embodiments 12-16, wherein the network includes a terminal row of optical switches, and each first and second output arm of each optical switch in the terminal row is in optical communication with a respective one of the one or more emitters.

Embodiment 18: The device of any one of Embodiments 1-17, wherein the one or more emitters are diffraction grating emitters.

Embodiment 19: The device of any one of Embodiments 1-18, further comprising one or more electrodes associated with the one or more emitters, wherein one or more of the electrodes is configured to record neural activity.

Embodiment 20: The device of any one of Embodiments 1-18, wherein adjacent emitters are located within a distance of one another that is less than or equal to a wavelength of the light.

Embodiment 21: The device of any one of Embodiments 17-19, wherein the network is at least a 1×8 network, the one or more emitters is a plurality of emitters spaced from the terminal row of optical switches by less than 4 mm, and the distal portion is within 2 degrees Celsius of ambient temperature when at least half of the emitters are emitting the light.

Embodiment 22: The device of any one of Embodiments 1-21, wherein the distal portion has a probe length less than 5.000 mm.

Embodiment 23: The device of any one of Embodiments 1-22, wherein the distal portion has a probe length less than 1.000 mm.

Embodiment 24: The device of any one of Embodiments 1-23, wherein the distal portion has a probe length less than 200 μm.

Embodiment 25: The device of any one of Embodiments 1-24, wherein the distal portion has a probe length less than 100 μm.

Embodiment 26: A method, comprising: with a device according to any one of Embodiments 1-25, illuminating neural tissue of a subject. As described elsewhere herein, the illumination can be visible light; it can also be in the infrared or even ultraviolet range. Light having a wavelength of 473 nm (or approximately 473 nm) is considered particularly suitable, but is not a requirement. One may illuminate neural tissue with illumination of one, two, or more wavelengths. One may also illuminate different areas of neural tissue with illumination of different wavelengths and/or different intensities.

Embodiment 27: The method of Embodiment 26, wherein the illumination is effective to stimulate one or more neurons of the subject.

Embodiment 28: The method of Embodiment 26, wherein the illumination is effective to suppress, reduce, or eliminate stimulation of one or more neurons of the subject.

Embodiment 29: A waveguide for electromagnetic waves, comprising: an optical path written into a pattern, the pattern including a plurality of segments of the optical path and a plurality of stitch boundaries therein, wherein at each of the stitch boundaries at least one of the segments of the optical path is stitched together with another of the segments of the optical path, and, at at least some of the stitch boundaries, the optical path defines an outward taper having a maximum width greater than a width of the optical path at portions of the associated segments remote from the at least one of the stitch boundaries.

Embodiment 30: The waveguide of Embodiment 29, wherein the taper is configured to be adiabatic.

Embodiment 31: The waveguide of any of Embodiments 29-30, wherein the pattern includes one or more bends of the optical path, and, optionally, one of more of the bends defines a bending radius of 50 μm or less.

Embodiment 32: The waveguide of any of Embodiments 29-31, wherein the optical path has a total length in the range of from about 1 nm to about 10 m, preferably from about 3 cm to about 42 cm.

Embodiment 33: The waveguide of any of Embodiments 29-32, wherein the pattern is contained within an area of about 10 mm$^2$ or less, preferably about 6 mm$^2$ or less.

Embodiment 34: The waveguide of any of Embodiments 29-33, wherein the area has a length of about 6 mm and a width of about 1 mm.

Embodiment 35: The waveguide of any of Embodiments 29-34, wherein the optical path is configured to transmit electromagnetic radiation having a wavelength in the range of about 250 nm and about 6 μm.

Embodiment 36: The waveguide of any of Embodiments 29-35, wherein the optical path is configured to transmit broadband wavelengths.

Embodiment 37: The waveguide of any of Embodiments 29-36, wherein the waveguide exhibits a propagation loss of less than about 0.27 dB/cm.

Embodiment 38: The waveguide of any of Embodiments 29-37, wherein the optical path possesses a thermal tunability of about 21 μm per ° C.

Embodiment 39: The waveguide of any of Embodiments 29-38, further comprising a heater capable of thermal communication with the optical path.

Embodiment 40: The waveguide of Embodiment 39, wherein the heater is configured to thermally tune the optical path.

Embodiment 41: The waveguide of any of Embodiments 29-40, wherein the optical path comprises $Si_3N_4$.

Embodiment 42: The waveguide of any of Embodiments 29-41, wherein the optical path consists of $Si_3N_4$.

Embodiment 43: The waveguide of any of Embodiments 29-42, wherein the optical path comprises $SiO_2$.

Embodiment 44: The waveguide of any one of Embodiments 29-43, wherein the optical path is fabricated, at least in part, via an e-beam lithography process.

Embodiment 45: The waveguide of Embodiment 44, wherein the e-beam lithography process comprises multi-pass lithography.

Embodiment 46: The waveguide of any of Embodiments 29-45, wherein the optical path is chemically-mechanically planarized.

Embodiment 47: The waveguide of any of Embodiments 29-46, wherein the waveguide is incorporated into an imaging component.

Embodiment 48: The waveguide of Embodiment 47, wherein the imaging component comprises an Optical Coherence Tomography (OCT) component.

Embodiment 49: A microchip, comprising a reference arm that comprises the waveguide according to any of Embodiments 29-43.

Embodiment 50: The microchip of Embodiment 49, further comprising: an input in optical communication with the reference arm, the input configured to communicate electromagnetic radiation; and a splitter in communication with the input, the splitter configured to divert a first portion of the electromagnetic radiation to the reference arm and a second portion of the electromagnetic radiation to a sampling arm.

Embodiment 51: The microchip of Embodiment 50, further comprising a sampling arm.

Embodiment 52: A method, comprising: directing electromagnetic radiation through the waveguide of any of Embodiments 29-48.

Embodiment 53: A method of refurbishing an optical system, the method comprising replacing a reference arm of the optical system with the waveguide of any of Embodiments 29-48.

Although the disclosure has been described in detail, it should be understood that various changes, substitutions, and alterations can be made herein without departing from the spirit and scope of the disclosed embodiments as defined by the appended claims. It should also be understood that the embodiments disclosed herein can employ or otherwise incorporate features of other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed is:

1. A device, comprising:
a distal portion configured to be implanted in a brain of a subject, the distal portion comprising a phased array of emitters configured to emit light in the visible spectrum, wherein each emitter in the array is independently switchable to enable emission from a selected emitter; and
a proximal portion configured to be external to the brain of the subject while the distal portion is implanted, wherein the proximal portion includes at least one waveguide in optical communication with the phased array of emitters the at least one waveguide defining a cross-sectional width less than 500 nm, wherein the at least one waveguide is coupled to a heating element configured to adjust a phase of light within the at least one waveguide,
wherein the proximal portion comprises an optical switch having an input arm, a first output arm, and a second output arm, and wherein the heating element is configured to adjust the phase of light within the at least one waveguide, between the first output arm and the second output arm, at a switching speed faster than about 1 ms.

2. The device of claim 1, wherein the at least one waveguide comprises silicon nitride.

3. The device of claim 1, wherein the at least one waveguide comprises Si3N4 and has a polygonal cross-sectional geometry.

4. The device of claim 1, wherein the at least one waveguide defines at least a portion of the optical switch, and wherein the at least one waveguide is configured to direct light, responsive to the phase, into the first output arm, into the second output arm, or into both the first and second output arms.

5. The device of claim 4, wherein the optical switch is an interferometer, and the at least one waveguide defines arms of the interferometer.

6. The device of claim 4, wherein the optical switch comprises a cascaded network of optical switches that include a lead switch, in which network each optical switch except the lead optical switch has an input arm defined by an output arm of another one of the optical switches in the network, each optical switch in the network has first and second output arms that are each in optical communication with the one or more emitters, each optical switch is an interferometer, and each waveguide is coupled to a respective heating element configured to adjust the phase of the respective waveguide to independently switch emission from a selected emitter.

7. The device of claim 6, wherein the network includes a terminal row of optical switches, and each first and second output arm of each optical switch in the terminal row is in optical communication with a respective one of the one or more emitters.

8. The device of claim 1, wherein the one or more emitters are diffraction grating emitters.

9. The device of claim 1, further comprising one or more electrodes associated with the one or more emitters, wherein one or more of the electrodes is configured to record neural activity.

10. The device of claim 1, wherein the distal portion has a probe length less than one or more of 1.000 mm, 200 µm, or 100 µm.

11. The device of claim 1, wherein the phased array of emitters receives single wavelength light from an input fiber.

12. The device of claim 6, wherein a distance between the phased array of emitters and the cascaded network of optical switches is at least 4 mm.

13. The device of claim 1, wherein the heating element induces at least one of phase tuning or beam steering.

14. The device of claim 1, wherein the heating element adjust an imaging displacement.

15. The device of claim 10, wherein the distal portion has a probe length less than 1.000 mm.

16. The device of claim 1, wherein the phased array collectively produces single neuron excitation and recording resolution.

* * * * *